US007252946B2

(12) United States Patent
Szasz

(10) Patent No.: US 7,252,946 B2
(45) Date of Patent: Aug. 7, 2007

(54) NUCLEIC ACID DETECTION

(75) Inventor: Nora Szasz, Cambridge, MA (US)

(73) Assignee: Zoragen, Inc., Cambridge, MA (US)

( * ) Notice: Subject to any disclaimer, the term of this patent is extended or adjusted under 35 U.S.C. 154(b) by 378 days.

(21) Appl. No.: 11/036,833

(22) Filed: Jan. 14, 2005

(65) Prior Publication Data

US 2005/0186601 A1  Aug. 25, 2005

Related U.S. Application Data

(60) Provisional application No. 60/622,522, filed on Oct. 27, 2004.

(51) Int. Cl.
*C12Q 1/68* (2006.01)
(52) U.S. Cl. .......................................................... 435/6
(58) Field of Classification Search ...................... None
See application file for complete search history.

(56) References Cited

U.S. PATENT DOCUMENTS

| | | | |
|---|---|---|---|
| 5,219,727 A | 6/1993 | Wang et al. | 435/6 |
| 5,601,976 A | 2/1997 | Yamane et al. | 435/6 |
| 5,639,611 A | 6/1997 | Wallace et al. | 435/6 |
| 5,641,268 A | 6/1997 | Martin et al. | 415/191 |
| 5,770,372 A | 6/1998 | Concannon | 435/6 |
| 5,942,391 A | 8/1999 | Zhang et al. | 435/6 |
| 5,952,170 A | 9/1999 | Stroun et al. | 435/6 |
| 5,972,602 A | 10/1999 | Hyland et al. | 435/6 |
| 6,174,681 B1 | 1/2001 | Halling et al. | 435/6 |
| 6,258,540 B1 | 7/2001 | Lo et al. | 435/6 |
| 6,664,056 B2 | 12/2003 | Lo et al. | 435/6 |
| 6,706,480 B1 | 3/2004 | Armour | 435/6 |
| 2001/0051341 A1 | 12/2001 | Lo et al. | 435/6 |
| 2004/0002093 A1 | 1/2004 | Shi | 435/6 |
| 2004/0106102 A1 | 6/2004 | Dhallan | 435/5 |
| 2004/0137470 A1 | 7/2004 | Dhallan | 435/6 |

FOREIGN PATENT DOCUMENTS

| | | |
|---|---|---|
| WO | WO91/08304 | 6/1991 |
| WO | WO93/18177 | 9/1993 |
| WO | WO93/18178 | 9/1993 |
| WO | WO93/22456 | 11/1993 |
| WO | WO95/08646 | 3/1995 |
| WO | WO95/16792 | 6/1995 |

OTHER PUBLICATIONS

Lo, et al., "Quantitative Analysis of Fetal DNA in Maternal Plasma and Serum: Implications for Noninvasive Prenatal Diagnosis", American Journal of Human Genetics (1998), V. 62, pp. 768-775.
Lo, et al., "Rapid Clearance of Fetal DNA from Maternal Plasma", American Journal of Human Genetics (1999), V. 64, pp. 218-224.
Ng, et al., "mRNA of Placental Origin is Readily Detectable in Maternal Plasma", Proceedings of the National Academy of Sciences (2003), V. 100, No. 8, pp. 4748-4753.

Chan, et al., "Size Distributions of Maternal and Fetal DNA in Maternal Plasma", Clinical Chemistry (2004), V. 50, pp. 88-92.
Herzenberg, et al., "Fetal Cells in the Blood of Pregnant Women: Detection and Enrichment by Fluorescence-Activated Cell Sorting", Proceedings of the National Academy of Sciences (1979), V. 76, No. 3, pp. 1453-1455.
Palomaki, et al., "Maternal Serum Screening for Down Syndrome in the United States: A 1995 Survery", American Journal of Obstetrics and Gynecology (1997), V. 176, No. 5, pp. 1046-1051.
Dhallan, et al., "Methods to Increase the Percentage of Free Fetal DNA Recovered from the Maternal Circulation", Journal of the American Medical Association (2004), V. 291, pp. 1114-1119.
Simpson, et al., "Cell-Free Fetal DNA in Maternal Blood", JAMA Editorial (2004), V. 291, No. 9, pp. 1135-1137.
Light, "Managed Care: False and Real Solutions", The Lancet (1994), V. 343, pp. 1197-1199.
Poon, et al., "Circulating Fetal DNA in Maternal Plasma", Clinica Chemica Acta (2001), V. 313, pp. 151-155.
Mansfield, "Diagnosis of Down Syndrome and Other Aneuploidies Using Quantitative Polymerase Chain Reaction and Small Tandem Repeat Polymorphisms", Human Molecular Genetics (1993), V. 2, pp. 43-50.
Bianchi, "Fetal Cells in the Maternal Circulation: Feasibility for Prenatal Diagnosis", British Journal of Hematology (1999), V. 105, pp. 574-583.
Jackson, "Fetal Cells and DNA in Maternal Blood", Prenatal Diagnosis (2003), V. 23, pp. 837-846.
Adinolfi, et al., "Prenatal Detection of Chromosome Disorders by QF-PCR", The Lancet (2001), V. 358, pp. 1030-1031.
Bischoff, et al., "Intact Fetal Cells in Maternal Plasma: Are They Really There?", The Lancet (2003), V. 361, pp. 139-140.
Chen, et al., "Microsatellite Alterations in Plasma DNA of Small Cell Lung Cancer Patients", Nature Medicine (1996), V. 2, No. 9, pp. 1033-1035.
Lo, et al., "Presence of Fetal DNA in Maternal Plasma and Serum", The Lancet (1997), V. 350, pp. 485-487.
Nawroz, et al., " Microsatellite Alterations in Serum DNA of Head and Neck Cancer Patients", Nature Medicine (1996), V. 2, pp. 1035-1037.
International Search Report (PCT/US05/01182).

*Primary Examiner*—James Martinell
(74) *Attorney, Agent, or Firm*—Kathleen M. Williams; Jeffrey Kopacz; Edwards Angell Palmer & Dodge

(57) ABSTRACT

The invention relates to methods for the detection of the amount of a nucleic acid in a sample. The described methods exploit the ability to physically pair nucleic acid molecules in a sample that have a reference sequence with nucleic acid molecules in the sample that have a target sequence. The presence of unpaired target or reference sequence following such physical pairing indicates a difference in the amount of the target sequence versus the reference sequence. The methods are broadly applicable for the determination of differences in the amounts of nucleic acids in diagnostic and research applications.

72 Claims, 5 Drawing Sheets

NUCLEIC ACID DETECTION

RELATED APPLICATIONS

This application claims the priority of U.S. provisional application No. 60/622,522, filed Oct. 27, 2004, and of U.K. application No. 0401739.9, filed Jan. 27, 2004, both of which are incorporated herein in their entirety.

FIELD OF THE INVENTION

This invention relates to the field of nucleic acid detection.

BACKGROUND OF THE INVENTION

The detection of small differences in nucleic acid content is an important task within the field of molecular diagnostics. However, this detection is difficult with current methods.

1 in 20 babies are born with a genetic disorder. Down syndrome is the most common chromosomal disorder affecting about 1 in 750 births (Table 1). The incidence of Down syndrome is increasing with the increasing average age at which women are bearing children.

TABLE 1

Incidence and inheritance of fetal aneuploidy.

| Disorder | Incidence | Inheritance |
| --- | --- | --- |
| Down syndrome | 1 in 750 births | Trisomy 21 |
| Edward syndrome | 1 in 3,000 births | Trisomy 18 |
| Patau syndrome | 1 in 5,000 births | Trisomy 13 |
| Klinefelter syndrome | 1 in 1,000 births | 47, XXY |
| Turner syndrome | 1 in 3,000 births | 45, XO |
| XYY syndrome | 1 in 1,000 births | 47, XYY |
| Triple-X syndrome | 1 in 1,000 births | 47, XXX |

Down syndrome is caused by trisomy 21—an occurrence of three instead of the normal two copies of chromosome 21. Down patients suffer from mental retardation, heart defects, premature death, and anatomical deformities; most require a lifetime of care. They pose an immense emotional, physical and financial strain on the families and society. Many women therefore want a choice about bringing a child with Down's syndrome into the world or to prepare emotionally for the birth.

Down syndrome is an example of a disease in which early detection is desirable. The tests used today are amniocentesis, chronic villus sampling (CVS), and maternal serum and ultrasound screens.

Amniocentesis is an invasive test requiring an ultrasound-guided needle biopsy of the amniotic fluid surrounding the fetus, through the mother's abdomen. Fetal cells from the amniotic fluid are cultured, and the chromosomes are visualized by fluorescent in-situ hybridization (FISH). Results take 2-4 weeks. Amniocentesis is only recommended between 15 and 18 weeks of pregnancy. It carries a 1% chance of miscarriage and a slight increase in risk of limb disorders. Amniocentesis is estimated to have a sensitivity of 99.3% and a specificity of 99.9%.

Serum screens for Down syndrome are non-invasive tests that measure the level of particalur serum markers. Markers include alpha-fetoprotein (AFP), human chronic gonadotropin (hCG), unconjugated estriol, inhibin A, and PAPP-A. Most markers are tested between the 16th and 18th week of pregnancy, and their combinations have less than 75% sensitivity at a 95% specificity.

In 1979 it was found that maternal blood contains fetal red blood cells (fRBC). In 1997, free fetal DNA was also found in maternal blood serum and plasma (U.S. Pat. No. 5,641, 268). These fetal cell and DNA, however, are diluted by significant amounts of maternal cells and DNA (Lo et al., J. Hum Genet. 1998 62, 768-75), complicating the detection of fetal genetic abnormalities.

Cystic fibrosis is a recessive genetic disease. Approximately 30,000 children and young adults suffer from the disease, and one in 31 adults carry a copy of the cystic fibrosis gene in the U.S. This means that one in about 3800 births suffer from cystic fibrosis, which increases to one in every 2,500 births for Caucasians.

Dominant diseases can be detected for a fetus in early pregnancy given a fetal DNA-containing sample, by looking for the presence or absence of the mutant dominant gene. Detecting recessive genetic diseases, such as cystic fibrosis, however, has been difficult because it is not enough to determine if a particular allele is present or not. Rather, it is necessary to determine if the fetus carries 1 or 2 copies of the mutant gene.

SUMMARY OF THE INVENTION

The invention relates to the pairing of target nucleic acid sequences with reference nucleic acid sequences, or with substitutes created in the same quantity, and the detection of unpaired nucleic acid sequences. The methods permit the determination of differences in the amounts of nucleic acid molecules.

In one aspect, the invention encompasses a method of determining the amount of a target nucleic acid relative to the amount of a reference nucleic acid in a nucleic acid sample, comprising: A) incubating the sample under conditions that permit specific binding of first and second probes to the target and reference nucleic acids, respectively, wherein (i) the nucleic acid sample comprises the target and reference nucleic acids; (ii) the first probe comprises a target nucleic acid binding sequence and a second probe binding moiety; (iii) the second probe comprises a reference nucleic acid binding sequence and a first probe binding moiety; B) placing the first and second probes under conditions that permit the pairing of the probes, wherein the pairing comprises binding of the first probe binding moiety to the second probe binding moiety, to form paired probes; and C) detecting unpaired probe, wherein the detecting is indicative of a difference in the amount of target and reference nucleic acids in the sample.

In one embodiment, the method further comprises removing un-hybridized probes after step (A).

In another embodiment, the method further comprises denaturing the hybridized probes after step (A).

In another aspect, the invention encompasses a method of determining the amount of a target nucleic acid sequence relative to the amount of a reference nucleic acid sequence in a nucleic acid sample, the method comprising: (a) providing a sample, the sample comprising the target nucleic acid sequence and the reference nucleic acid sequence; (b) contacting the sample, under conditions that permit hybridization, with first and second probes that have the following characteristics: (i) the first probe comprises a first binding partner moiety and a sequence that binds specifically to the target nucleic acid sequence, wherein the first binding partner moiety can bind a second binding partner moiety on the second probe when the probes are placed under conditions that permit binding of the binding partner moieties; and (ii) the second probe comprises a second binding partner moiety and a sequence that binds specifically to the reference nucleic acid sequence; (c) placing the first and second probes of step (b) under conditions that permit the first binding partner moiety of the first probe to interact with the second binding partner moiety of the second probe such that the first and second probes become bound to each other to form paired probes; and (d) detecting a probe that is not bound to another probe, wherein the detecting indicates a difference in the amount of target and reference nucleic acid sequences present in the sample.

In one embodiment, the method further comprises removing un-hybridized probes after step (b).

In another embodiment, the method further comprises denaturing the hybridized probes after step (b).

In another aspect, the invention encompasses a method of determining the amount of a target nucleic acid sequence relative to the amount of a reference nucleic acid sequence in a nucleic acid sample, the method comprising: (a) providing a sample, the sample comprising the target nucleic acid sequence and the reference nucleic acid sequence; (b) contacting the sample, under conditions that permit hybridization, with first and second probes that have the following characteristics: (i) the first probe comprises a first binding partner moiety and a sequence that binds specifically to the target nucleic acid sequence, wherein the first binding partner moiety can bind a second binding partner moiety on the second probe when the probes are placed under conditions that permit binding of the binding partner moieties; and (ii) the second probe comprises a second binding partner moiety and a sequence that binds specifically to the reference nucleic acid sequence; (c) removing un-hybridized probes; (d) placing the first and second probes of step (b) under conditions that permit the first binding partner moiety of the first probe to interact with the second binding partner moiety of the second probe, such that the first and second probes become bound to each other to form paired probes; and (e) detecting a probe that is not bound to another probe, wherein the detecting indicates a difference in the amount of target and reference nucleic acid sequences present in the sample.

In one embodiment, the method further comprises denaturing the probe after step (c).

In another aspect, the invention encompasses a method of determining the amount of a target nucleic acid sequence relative to the amount of a reference nucleic acid sequence in a nucleic acid sample, the method comprising: (a) providing a sample, the sample comprising the target nucleic acid sequence and the reference nucleic acid sequence; (b) contacting the sample, under conditions that permit hybridization, a first probe and a second probe that have the following characteristics: (i) the first probe comprises a first binding partner moiety and a sequence that binds specifically to the target nucleic acid sequence, wherein the first binding partner moiety can bind a second binding partner moiety on the second probe in a 1:1 manner when the probes are placed under conditions that permit binding of the binding partner moieties; and (ii) the second probe comprises the second binding partner moiety and a sequence that binds specifically to the reference nucleic acid sequence; (c) removing un-hybridized probes; (d) denaturing the hybridized probes; (e) placing the first and second probes of step (b) under conditions that permit the first binding partner moiety of the first probe to interact with the second binding partner moiety of the second probe, such that the first and second probes become bound to each other to form paired probes; and (f) detecting a probe that is not bound to another probe, wherein the presence of a probe that is not bound to another probe indicates a difference in the amount of target and reference nucleic acid sequences present in the sample.

In another aspect, the invention encompasses a method of determining the amount of a target nucleic acid sequence relative to the amount of a reference nucleic acid sequence in a nucleic acid sample, the method comprising: (a) providing a sample, the sample comprising the target nucleic acid sequence and the reference nucleic acid sequence; (b) immobilizing the sample; (c) contacting the sample, under conditions that permit hybridization, with an equal amount of a first probe and a second probe that have the following characteristics: (i) the first probe comprises a sequence that binds specifically to the target nucleic acid sequence and a first binding partner moiety, wherein the first binding partner moiety can bind a second binding partner moiety on the second probe when the probes are placed under conditions that permit binding of the binding partner moieties; and (ii) the second probe comprises a sequence that binds specifically to the reference nucleic acid sequence and a second binding partner moiety; (d) removing un-hybridized probes; (e) denaturing the hybridized probes; (f) placing the probes of step (e) under conditions that permit the first binding partner moiety of the first probe to interact with the second binding partner moiety of the second probe, such that the first and second probes become bound to each other to form paired probes; and (g) detecting a probe that is not bound to another probe, wherein presence of a probe that is not bound to another probe indicates a difference in the amount of target and reference nucleic acid sequences present in the sample.

Unless otherwise noted, each of the following embodiments of the invention are applicable to each of the aspects described herein. In another embodiment of the aspects described herein (above or below), prior to the detecting, the method comprises the step of removing paired probes or rendering paired probes resistant to detection. In another embodiment, the step of removing paired probes or rendering paired probes resistant to detection comprises cross-linking the probes. In another embodiment, the cross-linking comprises U.V. cross-linking or chemical cross-linking.

In another such embodiment, the first or second probe comprises a chemically modified nucleotide. In another embodiment, the chemically modified nucleotide comprises a halogenated nucleotide. In another embodiment, the chemically modified nucleotide comprises a thiol modified nucleotide, an amino modified nucleotide, or a biotinylated nucleotide.

In another embodiment, the chemically modified nucleotide is present in one or both of the first or second binding partner moiety. In another embodiment, the chemically modified nucleotide permits cross-linking of the first and second binding partner moieties.

In another embodiment of the aspects described herein, the step of detecting a probe that is not bound to another probe (i.e., an unpaired probe) comprises PCR amplification of a probe, target or reference nucleic acid sequence.

In another embodiment of the aspects described herein, the step of detecting a probe that is not bound to another probe (i.e., an unpaired probe) comprises the steps of cross linking to each other probes that are bound to each other, and amplifying a probe sequence, wherein cross-linked probes are not amplified.

In another embodiment of the aspects described herein, the first and second probes comprise single stranded nucleic acids.

In another embodiment of the aspects described herein, the first probe and the second probe interact via an adapter molecule.

In another embodiment of the aspects described herein, the first and second probes do not comprise a detectable label.

In another embodiment of the aspects described herein, at least one of the first and second probe further comprises a detectable label.

In another embodiment of the aspects described herein, the first and second probes do not comprise a hairpin structure.

In another embodiment of the aspects described herein, the first or the second probe is resistant to nuclease cleavage.

In another embodiment of the aspects described herein, the sample is obtained at least partially from serum or plasma or a processed part thereof. In another embodiment, the sample is obtained at least partially from a biopsy specimen or a processed part thereof. In another embodiment, the sample is obtained at least partially from a biological fluid or a processed part thereof. Examples beyond serum and plasma include urine, blood, sputum, semen, cerebrospinal fluid, etc. In another embodiment, the sample is obtained at least partially from a swab or smear or a processed part thereof. In another embodiment, the sample is obtained at least partially from cell culture or a processed part thereof. In another embodiment, the sample is obtained at least partially from nucleic acid synthesis. In another embodiment, the sample is a mix of the above described nucleic acid sources, e.g. biological fluid or a processed part of thereof, swab, smear, cell, culture, or nucleic acid synthesis. In another embodiment, the serum or plasma is obtained from a pregnant woman, and the method detects a difference in the amount of a fetal nucleic acid sequence.

In another embodiment of the aspects described herein, the sample is obtained at least partially from or comprises RNA or cDNA. In another embodiment, the nucleic acid sample comprises genomic DNA.

In another embodiment of the aspects described herein, the pairing comprises the binding of the first and second probes to each other in a specific, predefined ratio. In one embodiment, the specific predefined ratio is 1:1.

In another embodiment of the aspects described herein, the nucleic acid sample is immobilized on a solid support.

In another embodiment of the aspects described herein, the first probe and the second probe (e.g., target and reference probes) are contacted with the nucleic acid sample sequentially.

In another embodiment of the aspects described herein, the first and second probe binding moieties comprise nucleic acid sequences that can hybridize to each other under high stringency conditions.

In another embodiment of the aspects described herein, the sequence of the first probe binding moiety on the second probe is complementary to a sequence adjacent to the reference sequence in the nucleic acid sample.

In another embodiment of the aspects described herein, the second probe further comprises an additional tag moiety that can mediate selective binding to a solid support or to a specific binding partner.

In another embodiment of the aspects described herein, the step of detecting comprises immobilizing the second probe to a solid support via the additional tag moiety, whereby first probe that is bound to the second probe is selectively removed. In another embodiment, the solid support comprises a bead or particle. In another embodiment, the tag moiety is a member of a specific binding pair. In another embodiment, the tag comprises biotin.

In another embodiment of the aspects described herein, the step of placing the probes under conditions that permit the first binding partner moiety of the first probe to bind the second binding partner moiety of the second probe comprises one or more of placing the probes under conditions that permit hybridization, changing temperature, altering pH or salt concentration, and UV irradiation.

In another embodiment of the aspects described herein, the first or second probe comprises a fluorescent label. In another embodiment, the first and the second probes comprise a fluorescent label. In another embodiment, the first and/or second probe comprises a radioactive label.

In another embodiment of the aspects described herein, the detecting comprises capillary electrophoresis.

In another embodiment of the aspects described herein, the detecting comprises measurement of fluorescence, radioactivity or enzyme activity.

In another aspect, the invention encompasses a method of determining the amount of a target nucleic acid relative to the amount of a reference nucleic acid in a nucleic acid sample, the method comprising: (a) contacting a nucleic acid sample with a probe under conditions that permit hybridization, wherein the probe comprises a sequence that specifically binds to the target nucleic acid sequence and a sequence that specifically binds to the reference nucleic acid sequence; (b) detecting unhybridized probe, target or reference nucleic acid, wherein hybridized probe and/or target and/or reference nucleic acid is resistant to detection, and wherein the detecting determines the amount of the target nucleic acid relative to the amount of the reference nucleic acid present in the nucleic acid sample.

In one embodiment of the aspects described herein, the step of removing or rendering hybridized probes resistant to detection. In one embodiment, that step comprises cross-linking probe hybrids generated in step (a).

In another embodiment, the step of detecting comprises PCR amplification of an unhybridized probe, target or reference nucleic acid sequence.

In another embodiment of the aspects described herein, the step of detecting comprises the steps of cross linking hybridized probes to reference and target sequences to which they are hybridized, and amplifying a probe, reference or target sequence, wherein cross-linked sequences are not amplified.

In another aspect, the invention encompasses a method of detecting a chromosomal abnormality, the method comprising the steps of: (a) obtaining a nucleic acid sample; (b) contacting the sample, under conditions that permit hybridization, with first and second probes that have the following characteristics: (i) the first probe comprises a sequence that binds specifically to the target sequence, and a first binding partner moiety, wherein the first binding partner moiety can bind a second binding partner moiety on the second probe, when the probes are placed under conditions that permit binding of the binding partner moieties; and (ii) the second probe comprises a sequence that binds specifically to the reference sequence and the second binding partner moiety, wherein the first and second probes hybridize to target and reference nucleic acid sequences, respectively, present in the sample; (c) placing the hybridized probes under conditions that permit the binding partner moiety of the first probe to bind the binding partner moiety of the second probe, such that the first and second probes become bound to each other; and (d) detecting a probe that is not bound to another probe, wherein the detecting indicates a difference in the amount of target and reference nucleic acid sequences present in the sample, wherein the difference indicates the presence of a genetic abnormality.

In one embodiment, the method further comprises removing un-hybridized probes after step (b). In another embodiment, the method further comprises denaturing the hybridized probes after step (b).

In another embodiment, the nucleic acid sample is obtained from serum or plasma. In another embodiment, the serum or plasma is obtained from a pregnant woman and the method detects a chromosomal abnormality in her fetus. In one embodiment, the chromosomal abnormality is an anueploidy (non-limiting examples include Down syndrome, Edwards syndrome, Patau syndrome, Turner syndrome, triple X, Klinefelter syndrome, and XYY syndrome).

In another embodiment, the genetic abnormality is a chromosomal abnormality.

In another embodiment, the chromosomal abnormality is a chromosomal deletion or chromosomal duplication.

In another embodiment, the genetic abnormality is an autosomal recessive disorder, for example cystic fibrosis, congenital adrenal hyperplasia, and sickle cell anemia.

In another embodiment, the serum or nucleic acid is obtained from an individual suspected or known to have cancer. In another embodiment, the genetic abnormality is aneuploidy, chromosomal deletion or duplication associated with cancer.

In another aspect, the invention encompasses a method of detecting a chromosomal abnormality, the method comprising: (a) contacting a nucleic acid sample with a probe under conditions that permit hybridization, wherein the probe comprises a sequence that specifically binds to the target nucleic acid sequence and a sequence that specifically binds to the reference nucleic acid sequence; (b) removing or rendering hybridized probes generated in step (a) resistant to detection; and (c) detecting unhybridized probe, target or reference nucleic acid, wherein the detecting determines the amount of the target nucleic acid relative to the amount of the reference nucleic acid present in the nucleic acid sample.

In one embodiment, the nucleic acid sample is obtained from serum or plasma.

In another embodiment, the step of removing or rendering hybridized probes resistant to detection comprises cross-linking probe hybrids generated in step (a).

In another embodiment, the step of detecting comprises PCR amplification of an unhybridized probe, target or reference nucleic acid sequence.

In another embodiment, the step of detecting comprises the steps of cross linking hybridized probes to reference and target sequences to which they are hybridized, and amplifying a probe, reference or target sequence, wherein cross-linked sequences are not amplified.

In another aspect, the invention encompasses a kit for detecting a chromosomal abnormality, the kit comprising: (a) a first probe that comprises a sequence that binds specifically to a target sequence and a first binding partner moiety, wherein the first binding partner moiety can bind a second binding partner moiety on a second probe, when the probes are placed under conditions that permit binding of the binding partner moieties; and (b) a second probe that comprises a sequence that binds specifically to a reference sequence and the second binding partner moiety, wherein the first and second probes hybridize to target and reference nucleic acid sequences, respectively, present in a nucleic acid sample.

DETAILED DESCRIPTION OF THE INVENTION

Figure 1:
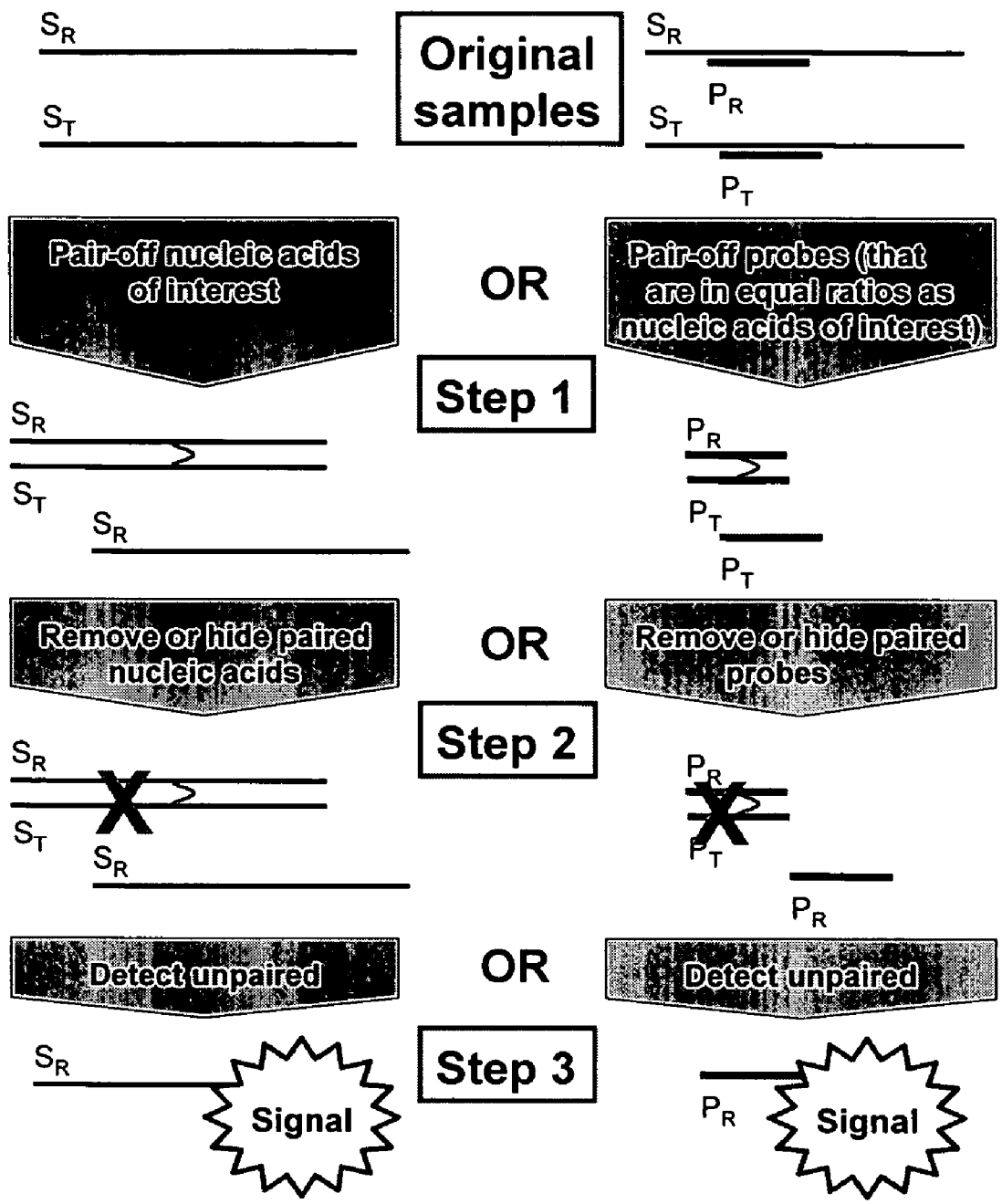
FIG. 1 shows a schematic of two approaches to the determination of a difference in the amount of a target nucleic acid as described herein. $S_R$ and $S_T$ are reference and target nucleic acids, respectively. $P_R$ and $P_T$ are reference and target probes, respectively. On the left side, a single probe embodiment is described: In Step 1, the fragmented reference and target nucleic acids are physically paired to each other. In Step 2, the paired nucleic acids are removed, hidden or sequestered, and in Step 3, the non-paired nucleic acid is detected. On the right side, a multiple probe embodiment is described: In Step 1, the reference and target probes are bound in amounts equal to the reference and target nucleic acid sample sequences, then the recovered probes are bound to each other. In Step 2, the paired nucleic acids are removed, hidden or sequestered, and in Step 3, the non-paired probes are detected.

Definitions:

As used herein, a "polynucleotide" or "nucleic acid" refers to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The term "polynucleotide" includes, without limitation, single- and double-stranded polynucleotide. The term "polynucleotide" as it is employed herein embraces chemically, enzymatically or metabolically modified forms of polynucleotide comprising, e.g., DNA, RNA, PNA, combinations of these and/or polymers containing one or more nucleotide analogs. A "nucleotide analog", as used herein, refers to a nucleotide in which the pentose sugar and/or one or more of the phosphate esters is replaced with its respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. Also included within the definition of "nucleotide analog" are nucleobase monomers which can be polymerized into polynucleotide analogs in which the DNA/RNA phosphate ester and/or sugar phosphate ester backbone is replaced with a different type of linkage. Further included within "nucleotide analogs" are nucleotides in which the nucleobase moiety is non-conventional, i.e., differs from one of G, A, T, U or C. Generally a non-conventional nucleobase will have the capacity to form hydrogen bonds with at least one nucleobase moiety present on an adjacent counter-directional polynucleotide strand or provide a non-interacting, non-interfering base.

"Polynucleotide" also embraces a short polynucleotide, often referred to as an oligonucleotide (e.g., a primer or a probe). A polynucleotide has a "5'-terminus" and a "3'-terminus" because polynucleotide phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a polynucleotide sequence, even if internal to a larger polynucleotide (e.g., a sequence region within a polynucleotide), also can be said to have 5'- and 3'-ends.

As used herein, the term "chemically modified," when used in the context of a nucleotide, refers to a nucleotide having a difference in at least one chemical bond relative to a standard ATP, CTP, GTP, UTP, dATP, dCTP, dGTP or dTTP nucleotide. The "chemical modification" does not refer to the modification occurring when a nucleotide is incorporated into a polynucleotide by 5' to 3' phosphodiester linkage.

As used herein, the term "hybridization" is used in reference to the physical interaction of complementary (including partially complementary) polynucleotide strands by the formation of hydrogen bonds between complementary nucleotides when the strands are arranged antiparallel to each other. Hybridization and the strength of hybridization (i.e., the strength of the association between polynucleotide strands) is impacted by many factors well known in the art including the degree of complementarity between the polynucleotides, and the stringency of the conditions involved, which is affected by such conditions as the concentration of salts, the presence of other components (e.g., the presence or absence of polyethylene glycol), the molarity of the hybridizing strands and the G+C content of the polynucleotide strands, all of which results in a characteristic melting temperature ($T_m$) of the formed hybrid.

As used herein, when one polynucleotide is said to "hybridize" to another polynucleotide, it means that the two polynucleotides form a hydrogen-bonded antiparallel hybrid under high stringency conditions. Hybridization requires partial or complete sequence complementarity between the polynucleotides that hybridize. When one polynucleotide is said to not hybridize to another polynucleotide, it means that there is insufficient sequence complementarity between the two polynucleotides to form a hydrogen-bonded hybrid, or that no hybrid forms between the two polynucleotides under high stringency conditions. As used herein, "specific hybridization" refers to the binding, duplexing, or hybrization of a nucleic acid molecule only to a target nucleic acid sequence and not to other non-target nucleic acid molecules in a mixture of both target and non-target nucleic acid sequence.

As used herein, the terms "low stringency," "medium stringency," "high stringency," or "very high stringency conditions" describe conditions for nucleic acid hybridization and washing. Guidance for performing hybridization reactions can be found in *Current Protocols in Molecular Biology*, John Wiley & Sons, N.Y. (1989), 6.3.1-6.3.6, which is incorporated herein by reference in its entirety. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); (2) medium stringency hybridization conditions in 6× SSC at about 45° C., followed by one or more washes in 0.2× SSC, 0.1% SDS at 60° C.; (3) high stringency hybridization conditions in 6× SSC at about 45° C., followed by one or more washes in 0.2× SSC, 0.1% SDS at 65° C.; and (4) very high stringency hybridization conditions are 0.5M sodium phosphate, 7% SDS at 65° C., followed by one or more washes at 0.2× SSC, 1% SDS at 65° C.

As used herein, a polynucleotide "isolated" from a sample is a naturally occurring polynucleotide sequence within that sample which has been removed from its normal cellular environment. Thus, an "isolated" polynucleotide may be in a cell-free solution or be placed in a different cellular environment.

As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

As used herein in the context of a sample, a sample that is obtained "at least partially" from a given source comprises at least one sample component obtained from such a source.

"Complementary" sequences, as used herein, refer to sequences in which antiparallel alignment juxtaposes A residues on one strand with T or U residues and G with C residues on the other strand such that A:T, A:U, and G:C hydrogen-bonded base pairs can form. These are the standard "Watson-Crick" base pairs occurring in the vast majority of DNA and RNA hybrids in vivo. As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. "Complementary" sequences can also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a double-stranded nucleic acid hybrid. A "fully complementary" hybrid has every nucleotide on one strand base paired with its juxtaposed counterpart on the opposite strand. In a "substantially complementary" hybrid, the two strands can be fully complementary, or they can include one or more, but preferably not more than 10 mismatched base pairs upon hybridization, while retaining the ability to hybridize under the conditions used in the methods described herein.

A "chromosomal abnormality", as used herein, refers to any deviation in the DNA composition or structure of a chromosome from that composition or structure most prevalent in a given population. This includes, but is not limited to, deletions, mutations, duplications, rearrangements, covalent modifications, uniparental disomy, and altered chromatin structure. The methods described herein are suited for detecting, among others, abnormal chromosome count (e.g. Down, Klinefelter, Patau, Edward, Turner, Triple-X, XYY, etc.) and abnormal sequence count (an abnormality where only a part of a chromosome is present in abnormal quantities).

The term "oligonucleotide" is defined as a molecule comprised of two or more deoxyribonucleotides and/or ribonucleotides, preferably more than three. Its exact size will depend upon many factors which, in turn, depend upon the ultimate function and use of the oligonucleotide. Oligonucleotides for use in the methods described herein are most often 15 to 600 nucleotides in length. The term "primer" as used herein refers to an oligonucleotide, whether occurring naturally as in a purified restriction digest or produced synthetically, which is capable of acting as a point of initiation of template-dependent nucleic acid synthesis. The primer may be either single-stranded or double-stranded and must be sufficiently long to prime the synthesis of the desired extension product in the presence of the chosen polymerase. The exact length of the primer will depend upon many factors, including hybridization and polymerization temperatures, source of primer and the method used. For example, for diagnostic applications, depending on the complexity of the target sequence, the oligonucleotide primer typically contains 15-25 or more nucleotides, although it may contain fewer or more nucleotides. The factors involved in determining the appropriate length of primer are readily known to one of ordinary skill in the art.

As used herein, "an individual" refers to a human subject as well as a non-human subject such as a mammal, an invertebrate, a vertebrate, a rat, a horse, a dog, a cat, a cow, a chicken, a bird, a mouse, a rodent, a primate, a fish, a frog, a deer, a fungus, a yeast, a bacteria, and a virus. The examples herein are not meant to limit the methodology of the present invention to a human subject only, as the instant methodology is also useful in the fields of veterinary medicine, animal sciences, research laboratories and such.

As used herein, "diagnosis" refers to the ability to demonstrate an increased likelihood that an individual has a specific condition or conditions. Diagnosis also refers to the ability to demonstrate an increased likelihood that an individual does not have a specific condition. More particularly "diagnosis" refers to the ability to demonstrate an increased likelihood that an individual has one condition as compared to a second condition. More particularly "diagnosis" refers to a process whereby there is an increased likelihood that an individual is properly characterized as having a condition ("true positive") or is properly characterized as not having a condition ("true negative") while minimizing the likelihood that the individual is improperly characterized with said condition ("false positive") or improperly characterized as not being afflicted with said condition ("false negative").

As used herein, the term "corresponding to" refers to a nucleotide in a first nucleic acid sequence that aligns with a given nucleotide in a reference nucleic acid sequence when the first nucleic acid and reference nucleic acid sequences are aligned. Alignment is performed, for example, by one of skill in the art using software designed for this purpose. As an example of nucleotides that "correspond," the nucleotide at position 51 of SEQ ID NO:6 of TCRB "corresponds to" nucleotide position 27,091 of Gen Bank Accession # GI:1552506 of TCRB, and vice versa. The term "corresponding" also refers, for example, to the relationship between two specific binding partners—that is, one member of a binding partner pair "corresponds to" the other member of such pair.

As used herein, the phrase "close to the amount of reference or target sequence present" when used in reference to probe concentration means that the concentration of the discussed probe or probes is equal within 80% to the concentration of the reference or the target sequence, whichever might be discussed.

As used herein, a "probe" refers to a type of oligonucleotide having or containing a sequence which is complementary to another polynucleotide, e.g., a target polynucleotide or another oligonucleotide. The probes for use in the methods described herein are ideally less than or equal to 600 nucleotides in length, typically between 40-600 nucleotides.

As used herein, the phrase "paired probes" refers to two probes that are physically associated with or bound to each other. Paired probes can be bound to each other by the association of two binding partner moieties as the term is defined herein, including, but not limited to binding via the formation of nucleic acid hybrids, binding via covalent chemical bonds, or binding via protein-protein interactions. The term "paired probes" encompasses not only probes that are paired in a 1:1 relationship, but also probes associated in higher order relationships, e.g., 1:2, 1:3, 1:4, 1:5, 1:6, 1:7, 1:8, etc. (i.e., one molecule of one probe pairing with 2, 3, 4, 5, 6, 7, or 8 molecules, etc. of a second probe), as long as the ratio is known or at least constant for a given set of probes. An "unpaired probe" is a probe (e.g., a first probe) that is not physically associated with or bound to another (e.g., a second) probe. The "pairing" can occur through one or more adapter molecules.

As used herein, the phrase "removing un-hybridized probes" means that probes not hybridized to target or reference nucleic acid are either physically removed from the solution or that they are rendered incapable of participating in later detection steps. By "removing" is meant that at least 80% of un-hybridized probe is removed, preferably at least 95%, 96%, 97%, 98%, 99% or more, up to and including 100%.

As used herein, the phrases "rendering hybridized probes resistant to detection" and "rendering paired probes resistant to detection" refer to the treatment of hybridized or paired probes such that they are not substantially detected in the nucleic acid detection method employed to detect unpaired probe. By "not substantially detected" is meant that hybridized or paired probes treated to render them resistant to detection contribute less than 10%, and preferably less than 2% of the signal in the nucleic acid detection method employed to detect unpaired probe. The phrase "rendering hybridized probes resistant to detection" is equivalent to the terms "hiding" or "sequestering" when applied to probes. Non-limiting examples of treatments that render hybridized probes resistant to detection include chemical and U.V.

cross-linking of probe to target or reference sequence or to another probe or the physical removal of said hybridized or paired probes.

As used herein, "binding partner" or "binding partner moiety" refers to a member of a specific binding pair. A specific binding pair is a pair of moieties that specifically bind to each other under a given set of conditions; "specific binding" refers to the binding of one member of the pair to the other member of the pair to the substantial exclusion of the binding of other moieties present in that environment.

As used herein, the phrase "conditions that permit a first binding partner moiety to interact with a second binding partner moiety" refers to those environmental conditions that favor the physical and/or chemical interaction of two members of a specific binding pair. Such conditions will vary depending upon the nature of the binding pair interaction, but can be determined by one of skill in the art. Exemplary conditions include hybridizing conditions as described herein or as known in the art, e.g., conditions of high stringency or below, when, for example, the binding partners are complementary nucleic acid sequences. Such conditions also include the substantial absence of competitor sequences, including sequences present in a nucleic acid sample for which the amount of a target sequence is to be determined. Within the methods described herein, the step of placing binding partner moieties or probes comprising them under conditions that permit a first binding partner moiety to interact with a second binding partner moiety can be performed as a separate step, e.g., following contacting probes with sample nucleic acids, or it can occur during such contacting.

As used herein, the term "target nucleic acid" refers to a polynucleotide whose amount is to be determined in a sample, relative to a "reference nucleic acid." A "target nucleic acid" contains a known sequence of at least 20 nucleotides, preferably at least 50 nucleotides, more preferably between 80 to 500 nucleotides but can be longer. A "target nucleic acid" of the invention can be a naturally occurring polynucleotide (i.e., one existing in nature without human intervention), or a recombinant polynucleotide (i.e., one existing only with human intervention), including but not limited to genomic DNA, cDNA, plasmid DNA, total RNA, mRNA, tRNA, rRNA. The target polynucleotide also includes amplified products of itself, for example, as in a polymerase chain reaction. As used herein, a "target polynucleotide" or "target nucleic acid" can contain a modified nucleotide which can include phosphorothioate, phosphite, ring atom modified derivatives, and the like. Target nucleic acid sequence necessarily differs from reference nucleic acid sequence, such that target and reference nucleic acid sequences cannot hybridize to each other under stringent conditions.

As used herein, the term "cross-linking" refers to covalent linkage of one probe to another, following a specific physical interaction between the two probes.

"Homology" or "identity" or "similarity" refer to sequence similarity between two nucleic acid sequences or between two polypeptide sequences. Homology can be determined by comparing a position in each sequence which may be aligned for purposes of comparison. When several positions of a compared sequence are occupied by the same bases or amino acids, then the molecules are homologous at that sequence. A degree of homology between sequences is a function of the number of matching or homologous positions shared by the sequences. An "unrelated" or "non-homologous" sequence shares less than 40% identity, though preferably less than 25% identity, with another sequence.

As used herein, the term "biological fluid" refers to a liquid taken from a biological source and includes, for example, blood, serum, sputum, lavage fluid, cerebrospinal fluid, urine, semen, sweat, tears, saliva, and the like.

As used herein, the phrase "resistant to nuclease cleavage" means that a given nucleic acid probe contains one or more chemical modifications or structural attributes that render it less susceptible to nuclease cleavage than a similar sequence without the modification or structural attribute. Non-limiting examples include changes to the phosphodiester linkages, e.g., the inclusion of a thiol linkage, and the presence of secondary structure, e.g., double-strandedness versus single strandedness over all or part of the probe molecule. By "less susceptible" is meant at least 10% fewer cleavage events relative to non-modified probe under the same nuclease cleavage conditions.

As used herein, the term "aneuploidy" refers to the state of having a chromosome number that is not a multiple of the haploid number for the species.

As used herein, "polymerase chain reaction" or "PCR" refers to an in vitro method for amplifying a specific polynucleotide template sequence. The PCR reaction involves a repetitive series of temperature cycles and is typically performed in a volume of 10-100 µl. The reaction mix comprises dNTPs (each of the four deoxynucleotides dATP, dCTP, dGTP, and dTTP), primers, buffers, DNA polymerase, and polynucleotide template. One PCR reaction may consist of 5 to 100 "cycles" of denaturation and synthesis of a polynucleotide molecule.

A "hairpin sequence", as used herein, comprises two self-complementary sequences that may form a double-stranded stem region, separated by a loop sequence. The two regions of the oligonucleotide which comprise the double-stranded stem region are substantially complementary to each other, resulting in self-hybridization. However, the stem can include one or more mismatches, insertions, side-loops, or deletions. The "hairpin sequence", as used herein, can additionally comprise single-stranded region(s) that extend from the double-stranded stem segment.

Description

Disclosed herein are methods that permit the detection of the amount of a target nucleic acid sequence. Generally, such detection is relative to the amount of a reference sequence. The methods described herein have broad applicability for both diagnostic and research purposes, wherever it is advantageous to determine the relative or absolute amount of a nucleic acid sequence. For example, the methods disclosed herein can be used to diagnose aneuploidies, such as occur in, for example, neoplastic cells and in individuals, e.g., fetuses or postpartum individuals or adults, afflicted with a genetic disorder.

In one aspect, the methods disclosed herein are applicable to the diagnosis of chromosomal abnormalities. Such methods include a method effective in detecting a difference in the amount of a target nucleic acid relative to the amount of a reference nucleic acid. Products which are representative of kits useful in diagnosing an individual as having a condition of interest are also disclosed.

The methods described herein exploit the ability to physically pair nucleic acid molecules in a sample that have a reference sequence with nucleic acid molecules in the sample that have a target sequence. The presence of unpaired target or reference sequence following such physical pairing indicates a difference in the amount of the target sequence versus the reference sequence. Because the physical pairing effectively removes an amount of target sequence equal or directly proportional to the amount of reference sequence, the method has sensitivity superior to prior art methods of determining the relative concentration of a nucleic acid sequence. To illustrate, where there are 20 units of reference sequence and 22 units of target sequence, a physical 1:1 pairing of target and reference sequences (other ratios are also applicable) effectively removes 20 units of target and reference sequence, permitting detection of just the remaining 2 units of target sequence. Through the physical pairing, then, the methods described herein can identify differences of less than one fold in the amounts of the target and reference sequences, potentially detecting differences as small as 5% or less. This sensitivity makes the method broadly applicable whenever one wishes to determine the amount of a target nucleic acid sequence in a sample. For example, the methods are applicable to the measurement of differential gene expression, which is often hampered by the lack of sensitivity of conventional methods below a difference of 2 fold.

It is noted that even if the steps of the techniques described herein are not perfectly efficient, resulting in only partial pairing and elimination of target:reference probe pairs, the method can still improve upon the accuracy of detection achievable with prior art methods. If one ends up with, for example, 15 units of sequence X and 5 units of sequence Y after pairing off, there is still a 3:1 ratio, which is detectable by standard PCR approaches.

In one aspect of the methods described herein, a difference in the amount of a target sequence is determined as follows. A sample comprising the target nucleic acid sequence and a reference nucleic acid sequence is contacted with first and second probes under conditions that permit hybridization to target and reference nucleic acid sequences that are present.

The first and second probes have the following characteristics:

i) the first probe comprises a first binding partner moiety and a nucleic acid sequence that hybridizes to the target nucleic acid sequence;

ii) the second probe comprises a second, corresponding binding partner moiety to the first binding partner moiety on the first probe, and a sequence that hybridizes to the reference nucleic acid sequence. The first and second corresponding binding partner moieties (which can be, but are not necessarily, substantially complementary nucleic acid sequences) on the respective probes can bind to each other when placed under conditions that permit such binding. Thus, when the probes are placed under conditions that permit binding between the first and second binding partner moieties, the probes become bound to each other via the binding partner interaction.

Subsequent detection of probes that are not paired indicates a difference between the amounts of reference and target nucleic acid sequences present in the sample. This approach is shown schematically in FIG. 1.

In one embodiment, after the probes are first hybridized to the target and reference sequences, unhybridized probes are removed or rendered inactive. One means of doing this is to wash away unhybridized probes. For this approach, it is advantageous, although not absolutely necessary, to immobilize the nucleic acid sample to a support. Probes can then be applied under hybridizing conditions, washing away the excess probes after they are permitted to hybridize. Probes can be added either simultaneously, with a single wash regimen, or, in the alternative, sequentially, with washing following each addition. The order will depend, in part, upon the nature of the binding partner moiety on the probes, in that some binding partner moieties may benefit from being kept apart from probes with corresponding binding partner until it is desired that the binding partners should interact—in these instances, for example, sequential probe binding can be favored over simultaneous probe binding. Following removal of the un-hybridized probes, the hybridized probes are placed under conditions that permit the respective binding partner moieties to bind to each other, followed by detection of probe molecules that are not bound to another probe.

In another embodiment, un-hybridized probe is not removed. This can be achieved, for example, by titrating the nucleic acid sample against the probes. Either a fixed amount of probe is hybridized with varying amounts of sample nucleic acid, or varying amounts of probe are hybridized with fixed amounts of sample nucleic acid. There will then be a probe or sample nucleic acid concentration at which the ratio of free target to reference sequences or ratio of free reference to target sequences is going to be maximized. By "free," is meant sequences without probes attached to them. At this probe concentration, the probe concentration used will approximately equal the lesser concentration of the target or the reference, and the relative amount of target and reference can be determined by the free sequence content.

In some embodiments, it is advantageous to cross-link probes to other probes or sequences. Probes can be cross-linked to other probes or sequences using any of a host of cross-linking methods. UV can cross-link nucleosides, albeit at low efficiencies. Introducing halogenated nucleosides can improve crosslinking efficiencies (Qiagen website). Other useful chemical modifications to nucleosides or nucleotides include, as non-limiting examples, thiolation, amidation and biotinylation. Chemical crosslinkers can also be used, like mitomycin C (Bizanek et al. Biochemistry 1992, 31, 3084-3091), nitric oxide (Caulfield et al. Chem Res Toxicology, 16(5):571-574, 2003), or pyrrole/imidazole CPI conjugates (Bando et al., J. Am. Chem. Soc., 2003, 125, 3471-3485).

After hybridization of the probes to the sample sequences or probes to each other, hybrids can be cross-linked using any of the methods described above, or techniques known in the art. The cross-linked hybrids are not effective templates for detection by, for example, PCR. Therefore, PCR using primers that amplify target and/or reference probes or sequences will yield amplification products only where there is non-cross-linked template sequence. As will be discussed below with regard to detection methods, amplification primers should be designed so they will either hybridize to the region at which probes become cross-linked or so that the amplification sequence would contain the cross-linked region, thus inhibiting PCR strand extension. In either instance the presence of cross-linked probe will interfere with PCR amplification, and therefore the readout of the PCR will correspond to the sequences not crosslinked through theses methods.

Figure 4:
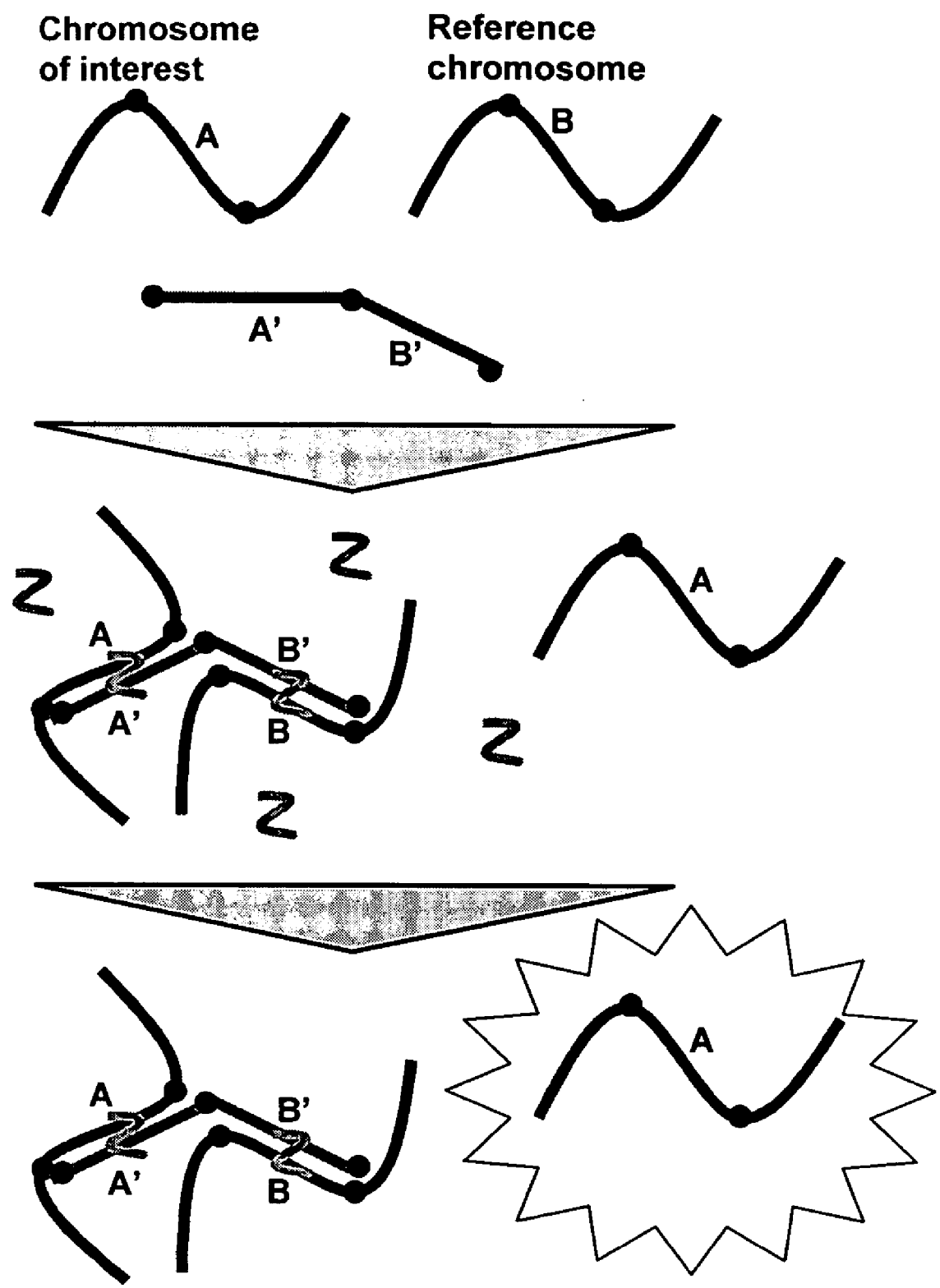
FIG. 4 shows a schematic of an embodiment of the methods described herein that uses a single probe. For this method, similar quantity (moles) of probe is added as the target or the reference sequence. Crosslinkers are then used to "hide" the bound nucleic acid sequences from detection, leaving only the excess unbound nucleic acid sequences to provide a detectable signal.
Figure 5:
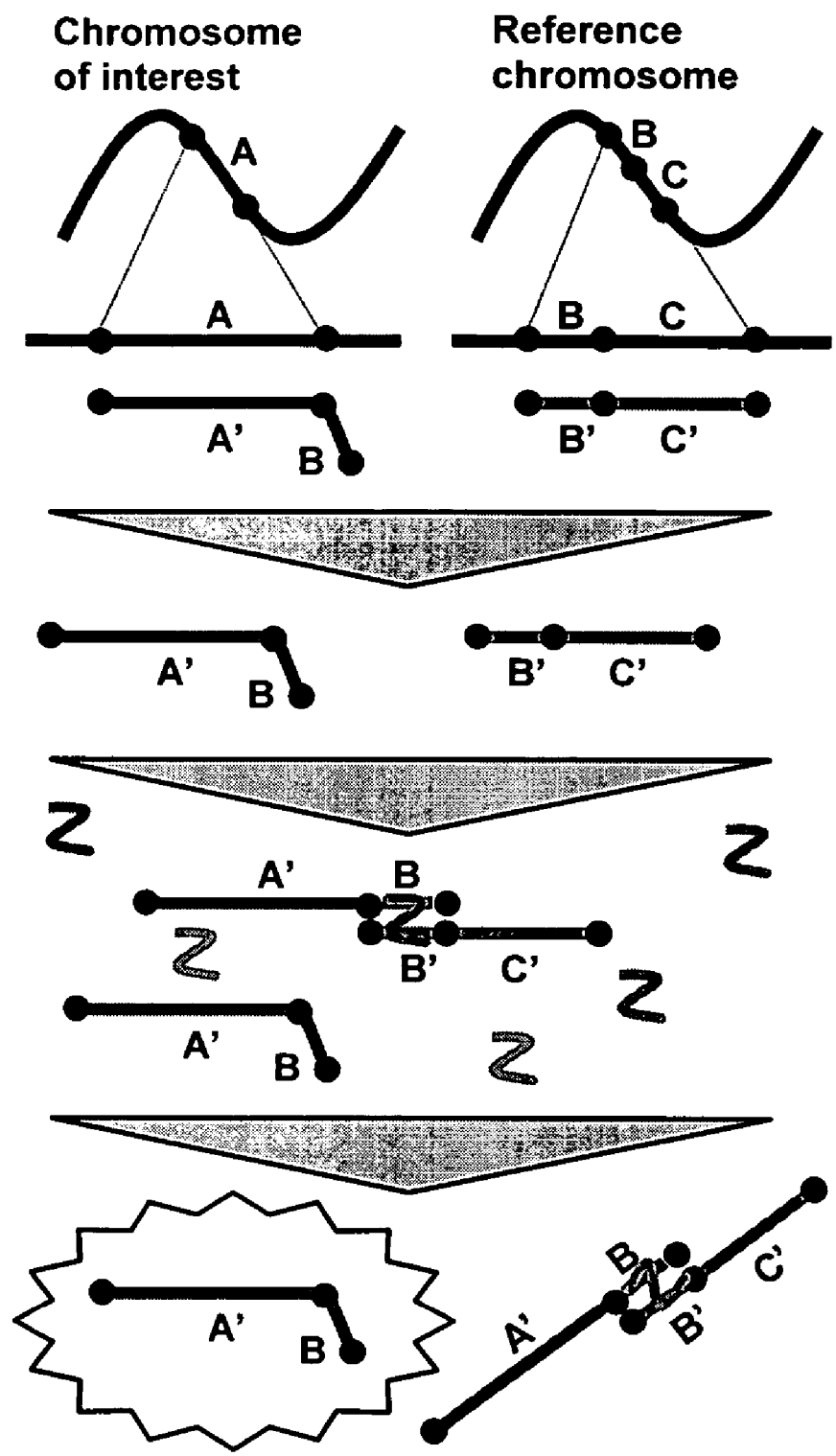
FIG. 5 shows a schematic of an embodiment of the methods described herein that uses chemical crosslinking of DNA duplexes instead of biotin removal for the two probe detection described in FIGS. 2 and 3. Similar to FIGS. 2 and 3, probes are recovered from the target and reference nucleic acid sequences and are then hybridized to each other. A crosslinker is then used to strongly crosslink the probes to each other. Later detection of unbound probes by e.g. PCR will not be able to amplify through the crosslinked region, providing a signal from the unbound probes only.

In another aspect, a single probe can be used to determine the amount of a target versus a reference sequence in a nucleic acid sample. In this aspect, the single probe has a region that specifically hybridizes to target sequence and a region that hybridizes to reference sequence. The single probe can be a single nucleic acid molecule or it can be two nucleic acid molecules physically joined to each other. In either instance, the single probe is characterized by the presence of binding regions for both target and reference sequences. In this aspect, the single probe is added to a nucleic acid sample in solution under conditions that permit hybridization. The hybridization of the single probe to target and reference sequences will pair the target and reference sequences to each other provided that the single probe is found in approximately the same or lower concentration as the lower concentration of the target and reference sequences (this can be achieved through titration). At this point, therefore, the unpaired target and reference sequences can be detected by previously described methods. An embodiment using cross-linking of a single probe to the sequence as a detection technique is shown schematically in FIG. 4. The single-probe aspect of the methods described herein is well suited for the situation, as found in blood serum, in which the nucleic acids tend to be present as short fragments. Thus, the single probe approach is well suited for use in detecting fetal abnormalities by evaluating maternal blood serum.

In further aspects, the methods described herein can be adapted for the parallel detection of multiple disorders. One approach is to simply run the same analyses with a set of different probes. Another approach would be to have a single multivalent reference probe comprise several (e.g., 2, 3 or more) different binding regions for different binding partners placed on several different target probes, each of which is specific for a different target sequence. The single reference probe construct would thus bind to several different target probes. This multi-specificity can be accomplished, for example, through use of a branched reference probe constructs (Shchepinov et al. Nucleic Acids Research, 1997, 25(22):4447-4454.) or probes clustered using multi-valent molecules (e.g. using PEG or avidin).

Another approach to the detection of multiple sequences in a single round would be to "daisy chain" the probes. In this approach, the reference probe has a binding partner moiety that binds a partner on the first target sequence probe, which in turn also has a binding partner moiety that binds a partner on a second target sequence probe, etc.

Further, combination of the multivalent probe approach and the "daisy chain" probe approach is contemplated as a means of further expanding the number of target sequences that can be evaluated in a given iteration of the methods described herein.

The various components and considerations for the methods described herein are described in further detail below.

Nucleic Acid Sample:

The nucleic acid sample to which the methods described herein are applied can be from any source. Frequently, the sample can be a biological material which is isolated from its natural environment and contains a polynucleotide. A sample can consist of purified or isolated polynucleotide, or it can comprise a biological sample such as a tissue sample, a biological fluid sample, or a cell sample comprising a polynucleotide. A biological fluid includes, as non-limiting examples, blood, plasma, sputum, urine, cerebrospinal fluid, ravages, and leukophoresis samples. A nucleic acid sample can be derived from a plant, animal, bacterial or viral source. Samples can be obtained from differing sources, including, but not limited to, samples from different individuals, different developmental stages of the same or different individuals, different diseased individuals (e.g., individuals with cancer or suspected of having a genetic disorder), normal individuals, different disease stages of the same or different individuals, individuals subjected to different disease treatment, individuals subjected to different environmental factors, or individuals with predisposition to a pathology, or individuals with exposure to an infectious disease agent (e.g., HIV).

Samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue or cells.

The sample preferably comprises isolated nucleic acid from a source as described above. Methods of isolating nucleic acids from biological sources are well known and will differ depending upon the nature of the source. One of skill in the art can readily isolate nucleic acid from a source as needed for the methods described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing.

In one embodiment, the sample is collected from a pregnant female, for example a pregnant woman. In this instance, the sample can be analyzed using the methods described herein to prenatally diagnose chromosomal abnormalities in the fetus. The sample can be collected from biological fluids, for example the blood, serum or some fraction thereof. In a preferred embodiment, the sample consists of purified nucleic acid isolated from the blood of a pregnant woman.

Analysis of blood plasma DNA has revealed that it is composed mainly of short DNA fragments, and interestingly, the average fragment size was greater in pregnant women than in nonpregnant women. Furthermore, it seems that fetal fragments in pregnant women's plasma DNA were shorter on average than maternal fragments (Chan et al., 2004, Clin. Chem. 50: 88-92). Methods for the isolation of nucleic acid from blood, serum or processed fractions thereof are well known in the art. Methods of isolation of nucleic acids from blood or serum are described in, for example Chen et al., 1996, Nature Med. 2: 1033-1035 and Lo et al., 1997, Lancet 350: 485-487. The Lo et al. reference specifically recognized the presence of fetal DNA in maternal plasma and serum. Further, Dhallan et al. (2004, J.A.M.A. 291: 1114-1119) and WO 95/08646 describe methods to enrich for fetal DNA from maternal serum. While such enrichment is not necessary for the prenatal diagnostic embodiments described herein, the potential for such enrichment could be advantageous in some aspects of the methods described herein.

In addition to the early detection of birth defects, the methods described herein can be applied to the detection of any abnormality in the representation of genetic sequences within the genome. It has been shown that blood plasma and serum DNA from cancer patients contains detectable quantities of tumor DNA (Chen et al., 1996, Nature Med. 2: 1035; Nawroz et al., 1996, Nature Med. 2: 1035-1037). Tumors are characterized by aneuploidy, or inappropriate numbers of gene sequences or even entire chromosomes. The detection of a difference in the amount of a given sequence in a sample from an individual can thus be used in the diagnosis of cancer.

Target Nucleic Acid:

The methods described herein facilitate the detection of differences in the amount of a target nucleic acid versus a reference nucleic acid sequence. Target nucleic acids include any nucleic sequence that is associated with a difference in sequence representation in healthy versus diseased individuals. Thus, a target nucleic acid sequence can be a sequence on a chromosome that is misrepresented in a disease, e.g., a sequence on a chromosome noted in Table 1.

Target sequences also include, for example, sequences known to exist in a polymorphic state. Target sequences can also include, for example, sequences known to be amplified or over-represented not in the whole individual, but in certain cells of the individual, as is seen for example, in cells of some cancers.

Finally, target sequences also include sequences under investigation, for example, for differential gene expression. The amount of an RNA transcript can be measured relative to a reference sequence by applying the methods described herein to a sample containing reverse-transcription reaction products of the RNA source of interest.

Reference Nucleic Acid:

The reference nucleic acid called for in the methods described herein is a sequence against which the amount of a target sequence is compared. Most often, a reference sequence will be one having a known or expected representation in the nucleic acid sample. For genomic DNA, for example, a reference sequence can be a sequence that is present in a single copy per genome, e.g., in heterozygous individuals, or in two copies, e.g., in homozygous individuals. Where the target sequence is to be measured in RNA, for example to determine the level of expression of a given message, the reference can be, for example, a housekeeping gene sequence, e.g., GAPDH, actin or a histone sequence, or another sequence for which the level is known, or at least which is known to be relatively invariant.

Most often, a reference sequence will be one that is already present in a biological sample, preferably at a known representation. For example, where one wishes to investigate the amount of a sequence associated with a genetic disorder, such as chromosome 21 trisomy indicative of Down syndrome, the reference sequence would be a sequence not present on chromosome 21, while the target sequence would be a sequence present on chromosome 21. In this example, where the reference sequence is present in two copies (a homozygous sequence), if the target sequence is found to be more abundant in maternal serum than the reference sequence using the methods described herein, the data would be indicative of Down syndrome in the fetus.

Alternatively, the reference sequence can be one that is spiked into the sample at a known or constant amount and which differs from the target sequence. This approach will give results that indicate the amount of target sequence relative only to the amount of external spiked reference sequence, but can be used to normalize between samples the levels of another reference sequence that is internal to the sample.

Generally it is preferred that the reference sequence have similar hybridization characteristics to the target sequence, at least in the region to which probe will bind, because it is advantageous for the probes to have similar hybridization characteristics under a single set of hybridization conditions. One of skill in the art can compensate, where necessary, for differences in hybridization characteristics by, for example, selecting a different reference sequence or by increasing or decreasing the length of the portion of the probe that binds the target or reference sequence so that hybridization efficiencies are similar.

Probes:

Probes for use in the methods described herein can have several different designs. In each instance, a probe will comprise a nucleic acid sequence that hybridizes to a target or reference nucleic acid sequence. It is preferred that each reference or target probe hybridize to a single place in the genome. As used herein, a "target binding sequence" refers to a sequence that hybridizes to a target nucleic acid. The "target binding sequence" is at least substantially complementary to the target nucleic acid. Likewise, as used herein, a "reference binding sequence" refers to a sequence that hybridizes to a reference nucleic acid. The "reference binding sequence" is at least substantially complementary to a reference nucleic acid. In certain applications, in particular when detecting a subtle difference in the nucleic acid sequence, for example in detecting Single Nucleotide Polymorphisms (SNPs), it is preferable that the target binding sequence be completely complementary to the target nucleic acid.

The nucleic acid of the probe can consist of DNA, RNA, PNA, combinations of these and/or polymers containing one or more nucleotide analogs. A "nucleotide analog", as used herein, refers to a nucleotide in which the pentose sugar and/or one or more of the phosphate esters is replaced with its respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. Also included within the definition of "nucleotide analog" are nucleobase monomers which can be polymerized into polynucleotide analogs in which the DNA/RNA phosphate ester and/or sugar phosphate ester backbone is replaced with a different type of linkage. Further included within "nucleotide analogs" are nucleotides in which the nucleobase moiety is non-conventional, i.e., differs from one of G, A, T, U or C. Generally a non-conventional nucleobase will have the capacity to form hydrogen bonds with at least one nucleobase moiety present on an adjacent counter-directional polynucleotide strand or provide a non-interacting, non-interfering base. Non-limiting examples of non-conventional nucleotide bases include deoxyinosine, R, Y, M, K, S, W, B, D, H, V, and N. Advantages of the use of modified or non-conventional nucleotides in probes (or, for that matter, in sample nucleic acids or adapter molecules) as described herein can include, for example, improved stability and modified sequence specificity.

Although there are a number of parameters to consider in designing the nucleic acid sequence to be used in a probe to specifically hybridize with a target or reference nucleic acid sequence, the design of such specifically-hybridizing probe sequences is routine in the art.

The portion of a probe useful in the methods described herein that is responsible for specifically hybridizing to reference or target nucleic acid in a sample will generally be from 40 to 600 nucleotides in length, although longer or shorter sequences are permissible. The portion of a probe that binds a target or reference sequence in a sample will preferably be between about 60-500 nucleotides in length, and more preferably between 80 and 400 bases. As a general rule, the longer the portion of the probe that binds the target or reference sequence, the more stringent the hybridization conditions can be. Also, it will often, although not always, be advantageous for the portions of respective target and reference probes that bind the respective target and reference sequences to be of similar length. Similar hybrid lengths will tend to ensure that reference and target sequences hybridize with similar efficiency under the same conditions.

As noted, there are exceptions to this general rule regarding similar lengths of probe reference and target sequences. For example, where the G+C content of the target and reference sequences varies considerably, it may be advantageous for the lengths of the portions of the probes that bind the reference and target sequences to differ in order to assure similar hybridization efficiencies under a given set of conditions. Of course, one could avoid or at least mitigate the need to manipulate probe length by selecting, where possible, a reference sequence having similar G+C content to the target sequence. Preferred G+C content is about 50%.

Specific binding of the probes to nucleic acid sequences is accomplished through specific hybridization. It will be appreciated by one skilled in the art that specific hybridization is achieved by selecting sequences which are at least substantially complementary to the target or reference nucleic acid sequence. Other conditions, such as physiologically relevant conditions as may be encountered inside an organism, can apply. The skilled artisan will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but preferably not more than 4, 3 or 2 mismatches per 100 base pairs upon hybridization, while retaining the ability to hybridize under the conditions most relevant to their ultimate application.

In certain applications, it is preferable to have probe sequences which are fully complementary to a target nucleic acid, e.g., when evaluating single nucleotide polymorphisms.

Additional parameters to consider in designing a probe sequence that hybridizes to a given target or reference sequence include, for example, nucleotide sequence and/or composition, hybridization temperature, buffer composition and potential for steric hindrance in the region to which the primer is required to hybridize.

As noted above, a positive correlation exists between probe length and both the efficiency and accuracy with which a probe will anneal to a target sequence. In particular, longer sequences have a higher melting temperature ($T_m$) than do shorter ones, and are less likely to be repeated within a given target sequence, thereby minimizing promiscuous hybridization.

As used herein, "$T_m$" and "melting temperature" are interchangeable terms which refer to the temperature at which 50% of a population of double-stranded polynucleotide molecules becomes dissociated into single strands. Formulae for calculating the $T_m$ of polynucleotides are well known in the art. For example, the $T_m$ may be calculated by the following equation: $T_m=69.3+0.41\times(G+C)\%-650/L$, wherein L is the length of the probe in nucleotides. The $T_m$ of a hybrid polynucleotide may also be estimated using a formula adopted from hybridization assays in 1 M salt, and commonly used for calculating $T_m$ for PCR primers: [(number of A+T)×2° C.+(number of G+C)×4° C.], see, for example, C. R. Newton et al. PCR, $2^{nd}$ Ed., Springer-Verlag (New York: 1997), p. 24. Other more sophisticated computations exist in the art, which take structural as well as sequence characteristics into account for the calculation of $T_m$. A calculated $T_m$ is merely an estimate; the optimum temperature is commonly determined empirically.

Probe sequences with a high G+C content or that comprise palindromic sequences tend to self-hybridize, as do their intended target sites, since unimolecular, rather than bimolecular, hybridization kinetics are generally favored in solution. However, it is also important to design a probe that contains sufficient numbers of G:C nucleotide pairings since each G:C pair is bound by three hydrogen bonds, rather than the two that are found when A and T (or A and U) bases pair to bind the target sequence, and therefore forms a tighter, stronger bond. Preferred G+C content is about 50%.

Hybridization temperature varies inversely with probe annealing efficiency, as does the concentration of organic solvents, e.g. formamide, that might be included in a hybridization mixture, while increases in salt concentration facilitate binding. Under stringent annealing conditions, longer hybridization probes, or synthesis primers, hybridize more efficiently than do shorter ones, which are sufficient under more permissive conditions. Preferably, stringent hybridization is performed in a suitable buffer under conditions that allow the reference or target nucleic acid sequence to hybridize to the probes. Stringent hybridization conditions can vary (for example from salt concentrations of less than about 1 M, more usually less than about 500 mM and preferably less than about 200 mM) and hybridization temperatures can range (for example, from as low as 0° C. to greater than 22° C., greater than about 30° C., and (most often) in excess of about 37° C.) depending upon the lengths and/or the nucleic acid composition of the probes. Longer fragments may require higher hybridization temperatures for specific hybridization. As several factors affect the stringency of hybridization, the combination of parameters is more important than the absolute measure of a single factor. "Stringent hybridization conditions" refers to either or both of the following: a) 6× SSC at about 45° C., followed by one or more washes in 0.2× SSC, 0.1% SDS at 65° C.; and b) 400 mM NaCl, 40 mM PIPES pH 6.4, 1 mM EDTA, 50° C. or 70° C. for 12-16 hours, followed by washing.

Binding Partners:

In each instance, a probe will also comprise a region or moiety that permits the physical pairing of target and reference probes under certain conditions.

In the instance where a single probe sequence is used, the probe will comprise a region that hybridizes to target nucleic acid and a region that hybridizes to reference nucleic acid. In this instance, the moiety that permits the physical pairing of target and reference probes is the probe itself, as it bridges the target and reference sequences when it is hybridized simultaneously to each. As discussed above, e.g. this bridging can be made permanent by cross-linking the hybridized regions, thereby removing the target and reference sequences where bound and the bound bridged molecules from the pool that can be amplified by, e.g., PCR. The net effect is to leave those molecules that were not paired as the only molecules capable of amplification. Amplified product therefore indicates the presence of more of one sequence than the other. Such a probe can be single- or double-stranded.

Where two or more probes are used in methods described herein, the region or moiety (referred to as a "binding partner moiety") that permits physical pairing will comprise a means of specifically binding one probe (under certain conditions) to a probe that binds another nucleic acid sequence. This ability of a probe that hybridized to a target sequence to bind a probe that hybridized to a reference sequence permits the "removal" or sequestration of a proportional number of target and reference probes. This "removal" permits the detection of non-paired target or reference sequence that is indicative of a difference in the amount of one sequence versus the other in the nucleic acid sample.

In a preferred aspect, a region or moiety for binding a reference probe to a target probe is made by incorporating a corresponding member of a specific binding partner pair into each of a target and a reference probe. Binding partners can interact by, for example, hybridization (involving hydrogen bonding), protein interactions, covalent bonding, ionic bonding, van der Waals interactions and hydrophobic interactions. The binding partners will necessarily bind to each other with a well-defined stoichiometry. This is not to say that the binding partners bind with 1:1 stoichiometry. Rather, what is important is that the stoichiometry be known. For example, avidin binds biotin with up to 8:1 stoichiometry. However, the biotin:avidin stoichiometry actually observed can vary depending upon the influences of steric hindrances caused by the appended nucleic acid sequence(s). For a given biotinylated probe, however, the stoichiometry of avidin or streptavidin binding is expected to remain constant.

Binding partners useful in the methods described herein are preferably conditionally able to bind to each other. By "conditionally able to bind to each other" is meant that the binding of one partner to the other can be manipulated such that detectable binding only occurs when one wishes for it to occur. The conditional aspect can be manipulated by, for example, changing temperature, salt or some other physical or chemical parameter of the environment. For example, lowering the temperature of a solution below the $T_m$ for a nucleic acid binding pair renders the pair able to bind each other. Conditional binding can also be achieved by competition for the binding sites by easily "removable" competitors. By "removable" competitors is meant molecules that compete for the binding of the probes to each other, but that can be either physically removed or made inert when it is desired to permit the probes to bind to each other.

Conditional binding can also be achieved through the addition of a catalyst that causes binding. For example, the exposure of complementary sequences comprising halogenated nucleosides to UV can result in the covalent cross-linking of the sequences. Chemical cross-linking agents are also known to those of skill in the art.

In one embodiment, the binding partners are substantially complementary nucleic acid sequences comprises by the respective probes. These sequences can, advantageously, although not necessarily, be present 5' of the probe sequence that specifically hybridizes to target or reference nucleic acid in the sample. In this aspect, the binding partner nucleic acid sequence on one probe is able to hybridize to the binding partner nucleic acid sequence on the other probe under a given set of conditions. Similar parameters to those considered in designing probe sequences are considered in designing the sequences of binding partner nucleic acid sequences to include on probes as described herein. For example, one of skill in the art will consider the impact of length and G+C content on the hybridization behavior of the binding partner sequences. Often, although not necessarily, the binding partner sequence of a probe that uses a nucleic acid as a binding partner will be of equal or shorter (e.g., at least one nucleotide or more shorter) length than that portion of a probe that binds the reference or target sequence.

Figure 2:
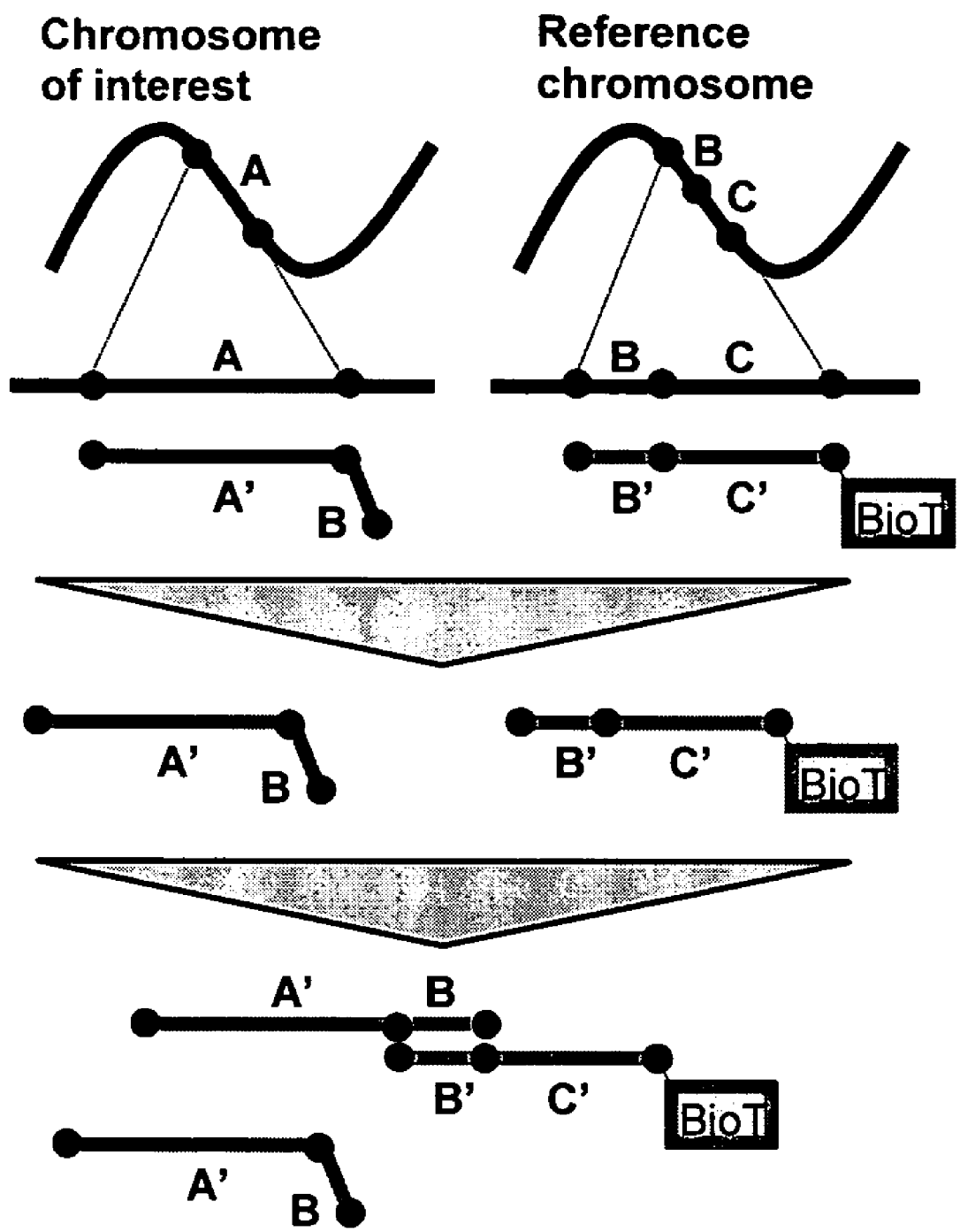
FIG. 2 shows a schematic of probes and binding partner sequences useful in one aspect of the methods described herein. Sequence A is a 49-mer target sequence on chromosome 21. Sequence B-C is an 49-mer reference sequence on chromosome 10. Sequence B is a 20-mer, and sequence C is a 29-mer. A' is complementary to A. A'-B is test probe. B'-C' is complementary to B-C. BioT is a biotin tag, and B'-C'-BioT is the reference probe. Probes A'-B and B'-C'-BioT are contacted with nucleic acid sample under hybridizing conditions. The probes are then recovered and hybridized to each other through the B and B' sequences.
Figure 3:
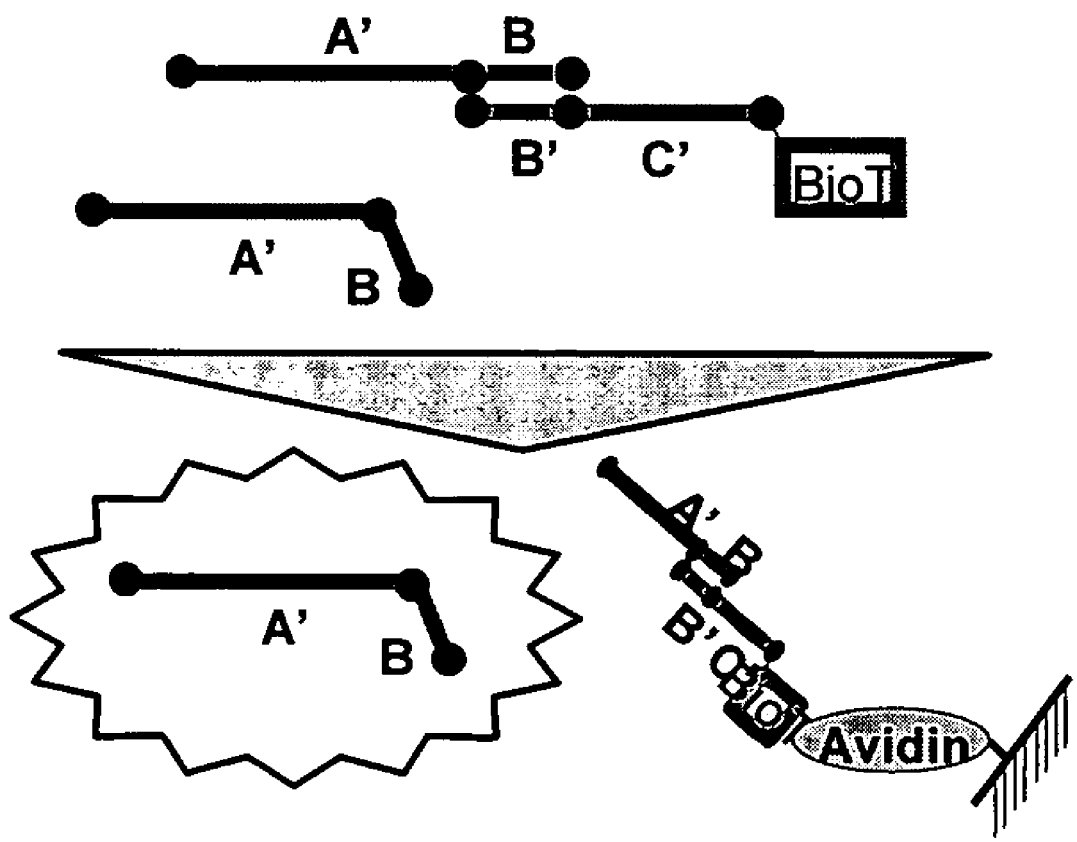
FIG. 3 shows a schematic of the steps following the hybridization shown in FIG. 2. The biotin tag is then used to remove the reference probe and target probe paired with it by binding to immobilized avidin. Remaining target probes are then detected.

In a related aspect, it can be advantageous for a nucleic acid sequence on one probe that binds a substantially complementary sequence on the other probe to also bind sequence adjacent to the sequence in the sample nucleic acid that it normally binds to. An advantage of this arrangement is that the target and reference probes can be contacted with the sample nucleic acid serially. Adding first the probe with the extra sequence and washing away all excess probes will result in all those extra sequences that would normally bind the second probe to be hidden by hybridization to the sample nucleic acid. Adding the second probe then hybridizes it to the sample nucleic acid, and does not create premature binding to the other probe. After washing away the excess second probe and recovering the bound probes e.g. through heating, the probes can then hybridize to each other. This is illustrated in FIG. 2. For example, where a target sequence is designated A, reference sequence is designated C, and a sequence adjacent to C on the nucleic acid comprising reference sequence C is termed B, a target probe can have sequence A'-B (where the "prime" indicates substantial complementarity), and a reference probe can have sequence B'-C'. Because sequence B is adjacent to C on the same reference nucleic acid molecule, hybridization reaction kinetics will favor the reference probe B'-C' binding to reference nucleic acid (B-C) rather than the B' portion of the reference probe binding to the B portion of the target probe. Target probe A'-B will bind the target nucleic acid via sequence A. If B'-C' was added first and the excess was washed away, the B' portion of the reference probe will not bind the B portion of the target probe while reference nucleic acid is present because the reference B'-C' probe has already hybridized over the full length of B-C, which kinetically favors B'-C' probe binding over binding between just the B and B' portions of the target and reference probes. Following the hybridization of the probes to the sample nucleic acid, the hybridized probes are isolated and again placed under hybridizing conditions. At this point, there is no competing reference nucleic acid present, so the B and B' portions of the respective probes are free to bind each other, thereby physically pairing the reference and target probes to each other. Detection of unpaired probes will indicate a difference between the amounts of reference and target nucleic acid sequences in the sample.

Binding partners can alternatively be respective members of any specific binding pair that is compatible with the environment required for nucleic acid hybridization. That is, the binding partner moieties can also interact through means other than hybridization. For example, the binding partner moieties can be a pair of moieties that bind to each other through covalent or non-covalent interactions. Examples of such binding partner moieties include but are not limited to: biotin-streptavidin, biotin-avidin, receptor-ligand pairs, heterodimerization motif pairs (e.g., complementary leucine zipper motifs, complementary helix-loop-helix motifs, etc.), antigen-antibody interactions, aptamer-ligand interactions, or multi-component chemical reactions. Methods for the linkage of non-nucleic acid binding partners to probes are well known in the art. Further, one skilled in the art can readily determine whether the environment required for nucleic acid hybridization has an adverse effect on the binding partner moieties or their abilities to bind each other.

The binding partner moieties can also interact indirectly through an "adapter molecule." As used herein, an adapter molecule is any molecule which is capable of binding specifically to the binding partner moieties, thereby bridging the reference and target probe sequences. In one embodiment, the adapter molecule comprises nucleic acid sequences that can hybridize to nucleic acid binding partner moieties of the first and second probe. The adapter molecule can be single-stranded, double-stranded or double-stranded with one or more overhangs. As one non-limiting example of an adapter, a double stranded nucleic acid with two different single-stranded overhangs could be used—one overhang would be substantially complementary to a binding partner sequence on the target probe, and the other would be substantially complementary to a binding partner sequence on the reference probe. The adapter molecule can also comprise multiple nucleic acids.

When using an adapter molecule, it is preferable that the sites which interact with the binding partner moieties are able to distinguish between the binding partner moieties of the first and second probe. It is also preferable that the ratio of first and second probes with which each adapter molecule can interact be a defined number. In one embodiment, the adapter molecule is able to bind the first and second probe at a ratio of 1:1.

It is not necessary that an adapter molecule interact with the first and second probes at a 1:1 ratio. In alternative embodiments, a single adapter molecule can bind to multiple copies (e.g., 2, 3, 4, 5, 6, 7, 8, etc.) of the first and second probes. For example, the adapter molecule can comprise a solid support containing a plurality of sites with which the first and second probes can specifically interact. As a non-limiting example, the binding partner moiety of the first probe may consist of a poly-A tail, and the binding partner moiety of the second probe may consist of a poly-C tail. The adapter molecule can comprise a solid support, for example a bead, comprising a plurality of poly-T and poly-G oligonucleotides, to which the first and second probe can specifically interact through their binding partner moieties, respectively. In another alternative embodiment, more than one (e.g., 2, 3, 4, 5, 6, 7, 8, etc.) adapter molecule can be employed.

Removal of Non-Hybridized Probes:

In some embodiments, it is advantageous to remove non-hybridized target and reference probes following hybridization to the nucleic acid sample. As noted above, one way to accomplish this is to immobilize the nucleic acid sample before hybridization and then wash away non-hybridized probes after they are hybridized to the immobilized nucleic acid sample. Methods for the immobilization of nucleic acid sample molecules are well known in the art. Immobilization can be accomplished using non-sequence-specific binding of the nucleic acid to a solid surface, for example, binding to nitrocellulose or nylon membrane, gels or microparticles. Alternatively, if desired, the immobilization can be mediated through sequence-specific interaction, e.g., by binding sample nucleic acid to beads or membranes comprising a polynucleotide molecule complementary to at least a portion of a sample nucleic acid sequence. Sequence-specific interaction can be mediated, for example, by oligonucleotide linkers ligated onto nucleic acid molecules in the sample. Alternatively, where the sample comprises mRNA, sample nucleic acid molecules can be immobilized by interaction with immobilized polyA sequences.

Where sample nucleic acid is immobilized, the non-hybridized probes can be washed away using an appropriate combination of wash buffer and temperature. For example, washes can be performed using hybridization buffer lacking probe at the same temperature used for probe hybridization. Preferably, however, the stringency of the washing can be increased by washing at higher temperature and in buffer containing reduced salt relative to hybridization buffer. For example, one to several (e.g., 2, 3, 5, etc.) washes can be performed at 65° C. in 1×SSC, 1% SDS followed by several (e.g., 2, 3, 5, etc.) washes in 0.1× SSC, 0.1% SDS at 65° C.

Other means of removing non-hybridized probes include, for example, nuclease degradation using a nuclease specific for single-stranded molecules. Examples include S1 nuclease of *Aspergillus oryzae*, and mung bean nuclease. Where nuclease digestion is used, sample nucleic acid need not necessarily be immobilized. The conditions for digestion with particular single-strand-specific nucleases are known in the art and can be adjusted with a minimum of experimentation by one of skill in the art. Factors to consider are buffer composition, duration of the digestion, enzyme composition, specificity, and efficiency. It is important to note that where, for example, PCR is to be used to ultimately detect the presence of un-paired probes in the methods described herein, one need not necessarily degrade an entire non-hybridized probe molecule in order to render it an ineffective template for subsequent amplification—one need only cleave it either at a sequence to which a PCR primer must bind, or anywhere in between the primer binding sites. Therefore, the digestion to remove non-hybridized probe, if this approach is taken, can be limited digestion.

Probe Recovery:

After the hybridization of the probes to the nucleic acid samples and the optional removal of excess probes, the probes can be unhybridized and recovered from the nucleic acid samples if desired. This step is not required. Probe recovery from the nucleic acid sample can be achieved, for example if the nucleic acid sample has been immobilized, by heating and recovering the supernatant. Alternatively, the probes could be used in their duplex form with the hybridized nucleic acid sequence.

Sequestration or Removal of Target:Reference Probe complexes:

The methods described herein exploit the formation of complexes between a reference probe and a target probe. After hybridization of target and reference probes to a nucleic acid sample (or after washes or probe recovery, where employed), target and reference probes are bound to each other via a binding partner interaction as described herein above. In order to detect non-complexed or "left over" probe molecules after the probes are bound to each other, it can be advantageous to remove, "hide" or sequester the target:reference probe complexes. There are several ways to accomplish this removal, "hiding" or sequestration.

In one approach, one of the probes, preferably the reference probe, has an additional binding moiety that permits it to be pulled out of solution onto a solid support. An example of such a binding moiety is biotin, which specifically binds avidin and streptavidin. Biotinylation of nucleic acid molecules is well known in the art and can be readily accomplished by one of skill in the art. When a binding moiety such as biotin is to be used to remove target:reference probe complexes, the method can proceed, for example, as follows: a) hybridize target probe and biotinylated reference probe to the sample nucleic acid; b) optionally remove non-hybridized target and reference probes; c) bind target and reference probes that hybridized to sample nucleic acid to each other; d) bind the target:reference probe complexes generated in step (c) to immobilized streptavidin or avidin; e) detect unpaired probe remaining in solution. The immobilized avidin or streptavidin can be immobilized on, for example, a bead, membrane or surface such as the surface of a test tube or multiwell plate well. An example of beads for this approach includes streptavidin-coated beads from Bangs Laboratories, Inc., product code: CP01N/5823, which are uniform microspheres, 0.95 mm in diameter, polymer: streptavidin coated microspheres, 1% solids. By passing the solution over the surface or by mixing the beads with the solution, one can pull biotin-containing probe molecules and other probes complexed to them out of solution. This removal can facilitate the detection of those non-complexed probes that remain in solution.

Another approach is to "hide" the target:reference probe complexes from detection. This can be achieved by permanent crosslinking of the target:reference probes in such a way that it interferes with the detection method. For example, if PCR is used for the detection of unpaired probes, complementary sequences on the target and reference probe can be used to bind them and this duplex can be crosslinked by chemical or physical means, such as UV, mitomycin C, or others described previously. If the primers for the detection are designed to overlap the permanent crosslink site or can be found on opposite sides of the crosslink sites, PCR amplification of paired probes will be inhibited, thus only unpaired probes will be amplified, and thus detected.

Detection of Unpaired Probes:

Following the physical pairing of target and reference probes in proportion to the amount of target sequence present, the methods described herein require the detection of unpaired probes. This detection can be performed by one of several different approaches.

One method of detecting unpaired probe uses polymerase chain reaction (PCR) amplification of probe molecules that are available to serve as amplification templates. PCR is well known in the art, and uses a thermostable template dependent polymerase and oligonucleotide primers that anneal to template nucleic acid on opposite strands in cycles of primer annealing, primer extension and strand separation to generate exponentially increasing numbers of duplicate copies of a template sequence. See, for example, Mullis et al., U.S. Pat. No. 4,683,202.

PCR detection of unpaired probes can be performed through use of PCR primers that amplify the unpaired probe sequences. PCR primers can be designed so as to exploit the nature of the unpaired probes. For example, where the target and reference probes bind to each other through hybridization of complementary sequence tags, one of the primers used for unpaired probe amplification can be designed to be complementary to the sequence tag. If, for example, the target and reference probes are cross-linked to each other after hybridization of the complementary sequence tags, the tags of the cross-linked molecules will not be available for amplification primer binding, which will exclude the cross-linked probes from amplification using a primer that hybridizes to the tag. Such an approach would leave only the unpaired probes available for amplification and subsequent detection.

The detection of PCR product indicative of unpaired probe and a difference in the amount of target nucleic acid can be by any means commonly used to detect PCR products. For example, PCR can incorporate a fluorescent or radiolabeled nucleotide or primer, and fluorescence or isotope detection can be used to obtain a read out. Alternatively, a real time method such as the TaqMan™ and Molecular Beacon methods, or related methods, can be used.

In the TaqMan assay (see e.g., U.S. Pat. No. 5,723,591), two PCR primers flank a central probe oligonucleotide. The probe oligonucleotide comprises two fluorescent moieties. During the polymerization step of the PCR process, the polymerase cleaves the probe oligonucleotide. The cleavage causes the two fluorescent moieties to become physically separated, which causes a change in the wavelength of the fluorescent emission. As more PCR product is created, the intensity of the novel wavelength increases.

Molecular Beacons (see U.S. Pat. Nos. 6,277,607; 6,150,097; 6,037,130) are an alternative to TaqMan. Molecular Beacons undergo a conformational change upon binding to a complementary template. The conformational change of the Beacon increases the physical distance between a fluorophore moiety and a quencher moiety on the Beacon. This increase in physical distance causes the effect of the quencher to be diminished, thus increasing the signal derived from the fluorophore.

Other applicable fluorescent and enzymatic PCR technologies, such as Scorpions™ (Solinas et al., 2001, Nucleic Acids Res. 29: e96), Sunrise™ primers (Nazarenko et al., 1997, Nucleic Acids Res., 25, 2516-2521), and DNAzymes can also be used.

PCR-based detection of unpaired probes can also use capillary electrophoresis for rapid detection. Generally, where capillary electrophoresis is used, amplification of a sequence incorporates a fluorescent nucleotide or primer that is then detected as sample passes through the capillary.

Capillary electrophoresis can also be used without the need for PCR amplification if the signal from the unpaired probes is sufficient for a reliable signal. Alternatively, fluorescence tags or fluorescence tag "dockers" could be used that selectively bind unpaired probes. By fluorescence tag "dockers" are meant entities that can bind a predetermined number of fluorescent tags either directly or through adapter molecules to aid in detection. Yet another method is to add inactive enzymes that can be activated either directly, or through adapter molecules by the unpaired probes selectively. Enzyme activity can then be detected by a change in color, fluorescence or similar readout. Other detection methods could include radioactive tagging and other methods.

Chromosome Abnormalities and Disease:

In the methods described herein, deviations from a 1:1 ratio of target to reference gene indicates a likely chromosomal abnormality. Non-limiting examples of chromosome abnormalities that are associated with disease and which can be evaluated using the method according to the methods described herein are provided in Table 1 below.

TABLE 1

Chromosome Abnormalities and Disease

| Chromosome Abnormality | | Disease Association |
|---|---|---|
| X, Y | XO | Turner's Syndrome |
| | XXY | Klinefelter syndrome |
| | XYY | Double Y syndrome |
| | XXX | Trisomy X syndrome |
| | XXXX | Four X syndrome |
| | Xp21 deletion | Duchenne's/Becker syndrome, congenital adrenal hypoplasia, chronic granulomatus disease |
| | Xp22 deletion | steroid sulfatase deficiency |
| | Xq26 deletion | X-linked lymphproliferative disease |
| 1 | 1p- (somatic) monosomy | neuroblastoma |
| 2 | monosomy trisomy 2q | growth retardation, developmental and mental delay, and minor physical abnormalities |

TABLE 1-continued

Chromosome Abnormalities and Disease

| Chromosome | Abnormality | Disease Association |
|---|---|---|
| 3 | monosomy | |
| | trisomy (somatic) | non-Hodgkin's lymphoma |
| 4 | monosomy | |
| | trsiomy (somatic) | Acute non lymphocytic leukaemia (ANLL) |
| 5 | 5p- | Cri du chat; Lejeune syndrome |
| | 5q- (somatic) | myelodysplastic syndrome |
| | monosomy | |
| | trisomy | |
| 6 | monosomy | |
| | trisomy (somatic) | clear-cell sarcoma |
| | 7q11.23 deletion | William's syndrome |
| | monosomy | monosomy 7 syndrome of childhood; somatic: renal cortical adenomas; myelodysplastic syndrome |
| | trisomy | |
| 8 | 8q24.1 deletion | Langer-Giedon syndrome |
| 8 | monosomy | |
| | trisomy | myelodysplastic syndrome; Warkany syndrome; somatic: chronic myelogenous leukemia |
| 9 | monosomy 9p | Alfi's syndrome |
| | monosomy | |
| | 9p partial trisomy | Rethore syndrome |
| | trisomy | complete trisomy 9 syndrome; mosaic trisomy 9 syndrome |
| 10 | monosomy | |
| | trisomy (somatic) | ALL or ANLL |
| 11 | 11p- | Aniridia; Wilms tumor |
| | 11q- | Jacobson Syndrome |
| | monosomy (somatic) | myeloid lineages affected (ANLL, MDS) |
| | trisomy | |
| 12 | monosomy | |
| | trisomy (somatic) | CLL, Juvenile granulosa cell tumor (JGCT) |
| 13 | 13q- | 13q- syndrome; Orbeli syndrome |
| | 13q14 deletion | retinoblastoma |
| | monosomy | |
| | trisomy | Patau's syndrome |
| 14 | monsomy | |
| | trisomy (somatic) | myeloid disorders (MDS, ANLL, atypical CML) |
| 15 | 15q11–q13 deletion | Prader-Willi, Angelman's syndrome |
| | monosomy | |
| | trisomy (somatic) | myeloid and lymphoid lineages affected, e.g., MDS, ANLL, ALL, CLL) |
| 16 | 16q13.3 deletion | Rubenstein-Taybi |
| | monosomy | |
| | trisomy (somatic) | papillary renal cell carcinomas (malignant) |
| 17 | 17p- (somatic) | 17p syndrome in myeloid malignancies |
| | 17q11.2 deletion | Smith-Magenis |
| | 17q13.3 | Miller-Dieker |
| | monosomy | |
| | trisomy (somatic) | renal cortical adenomas |
| | 17p11.2–12 trisomy | Charcot-Marie Tooth Syndrome type 1; HNPP |
| 18 | 18p- | 18p partial monosomy syndrome or Grouchy Lamy Thieffry syndrome |
| | 18q- | Grouchy Lamy Salmon Landry Syndrome |
| | monosomy | |
| | trisomy | Edwards Syndrome |
| 19 | monosomy | |
| | trisomy | |
| 20 | 20p- | trisomy 20p syndrome |
| | 20p11.2–12 deletion | Alagille |
| | 20q- | somatic: MDS, ANLL, polycythemia vera, chronic neutrophilic leukemia |
| | monosomy | |
| | trisomy (somatic) | papillary renal cell carcinomas (malignant) |
| 21 | monosomy | |
| | trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| | monosomy | |
| | trisomy | complete trisomy 22 syndrome |

Generally, evaluation of chromosome or gene sequence dosage is performed in conjunction with other assessments, such as clinical evaluations of patient symptoms. For example, prenatal evaluation may be particularly appropriate where parents have a history of spontaneous abortions, still births and neonatal death, or where advanced maternal age, abnormal maternal serum marker results, or a family history of chromosomal abnormalities is present. Postnatal testing may be appropriate where there are multiple congenital abnormalities, clinical manifestations consistent with known chromosomal syndromes, unexplained mental retardation, primary and secondary amenorrhea, infertility, and the like.

EXAMPLES

Example 1

Detection of the Amount of a Chromosome 21 Sequence Relative to a Chromosome 10 Sequence Using Biotin Immobilization of the Reference The methods described herein were applied to the detection of trisomy 21 in maternal serum. The test and reference probes used were as follows:

Test probe:

(SEQ ID NO: 1)
5'-CGTGAAGTTCTGTGGACAGTAGTGCTTGTCTGTGGTCAGCCCTGGG

CTCAACGGGGCTGCCTCAGAGAAGCTGCTGAGGACCACCCAATCGACATT

GAG-3'

Reference Probe:

(SEQ ID NO: 2)
5'-[BioT]ACAAGCTGCAAGCTCACGACTTACCATTCCGTAACGCTT

TTATGGGCTCTGATGACCGAGGTCTCAATGTCGATTGGGTGGT-3'

The reference probe has a biotin tag at the 5' end. The last 20 nucleic acids of the test probe (bold) are the complement of the last 20 nucleic acids of the reference probe (flipped and complemented). In initial tests, the test probe was found to form a hairpin that interfered with its hybridization to target sequence. While these sequences could be adapted by modifying the hybridization conditions, e.g., by increasing the hybridization temperatures, alternative test and reference probes were designed as shown below. The alternative reference and test probes are still specific for similar regions of 10p and 21q, respectively.

Reference Probe:10p (SEQ ID NO: 3)
5'-[6-FAM]ACGCTTTTATGGGCTCTGATGACCGAGGTCTCAATGT

CGATTGGGTGGT[BioT]-3'

21q Test Probe (for Down):

(SEQ ID NO: 4)
5'-[6-FAM]TGGTACTTTTAGGGGAAAACGTGATGTGTGGACTGTAT

CCCAAGGCCTTACCACCCAATCGACATTGAG

X Test Probe (for Turner, Triple X, Klinefelter):

(SEQ ID NO: 5)
5'-[6-FAM]CTCTCTGCAAAGCCTCCTAGCCCGGTTCTCCAGCCCTC

CCCAGACCAATACCACCCAATCGACATTGAG

18 Test Probe (for Edward):

(SEQ ID NO: 6)
5'-[6-FAM]CCATGGGAACAGAGAAACCTGCGTGTGAGGTGTCAGCAT

GAGGAGACCAACCACCCAATCGACATTGAG

The 3' 20 nucleotides (bold) of the 10p reference probe are complementary to the 3' 20 nucleotides (bold) of each of the target probes. The complementary probe regions are an example of a binding partner pair useful in the methods described herein.

Each of these probes carry fluorescent tags, e.g., 6-FAM, permitting quantification by capillary electrophoresis for controls. The 6-FAM tags do not participate in the reactions.

The biotin label at the 3'-end of the reference probe can be used to remove paired probes.

In this method, one starts with high molecular weight genomic DNA, at relatively high concentration (>0.1 mg/ml) and a probe mix with appropriate primers.

A. Making the Filters

Denatured sample DNA is immobilized on nylon membrane (e.g., Osmonics Magna Nylon Transfer Membrane, 0.22 um, Material 1213441, Catalog# NOTHYA0010) after denaturation. Generally, one will use pieces of membrane of approximately 2-4 mm for each sample. Membranes should be marked so that multiple samples can be hybridized simultaneously.

DNA is applied to the membrane pieces as follows. DNA, e.g., 1 µg, is denatured by alkalai (NaOH) before spotting onto membranes, 1 µl at a time, allowing the membrane to dry between applications.

Membranes are dried and U.V. cross-linked (50 mJ, both sides). It can be helpful to photograph the membranes at this point on a piece of plastic wrap with markings below each membrane to ease later identification.

B. Pre-Hybridization and Hybridization

1. Membranes are prehybridized together in a screw-top centrifuge tube containing 1 ml of prehybridization solution (0.5M sodium phosphate pH7.2, 7% SDS, 1 mM EDTA, 100 µg/ml alkali-denatured herring sperm DNA), at 65° C. for 2 hrs to overnight.

2. Add 3 µl human Cot-1 DNA (1 mg/ml) to 300 µl of pre-hybridization solution and boil in a screw-top tube for 2 minutes.

3. Remove the prehybridization solution from the filters add in its place 200 µl of the solution boiled in step 2. Incubate for 30-60 minutes at 65° C.

4. Add 1 µl Cot-1 DNA (1 mg/ml) to 1 µl of probe mix, 2 µl *E. coli*/HaeIII DNA (at 3.5 mg/ml; to prepare, digest 500 µg *E. coli* genomic DNA with 50 U HaeIII, in a total of about 0.5 ml 1× ReAct 2 (BRL). Phenol extract, ethanol precipitate and redissolve in $H_2O$ to 3.5 mg/ml), 2 µl FX174/HaeIII (at 250 µg/ml) and 1 µl of a mix containing final concentrations of 20 µM each blocker primer. Denature by adding 2 µl 1 M NaOH and incubating at 37° C. for 1 minute. Then place on ice and add 3 µl 1M $NaH_2PO_4$; mix, and add to the tube of step (3). Incubate overnight at 65° C.

C. Post-Hybridization Washes and PCR

1. Remove hybridization mix and rinse membrane pieces once with 1 ml prehybridization solution. Transfer membrane pieces to a 50 ml centrifuge tube. Wash at 65° C. in (1) 1× SSC, 1% SDS, (use a total of 500 ml, prewarmed to 65° C.) followed by (2) 500 ml of 0.1× SSC, 0.1% SDS, 65° C. Washes should be performed with agitation between frequent solution changes, for a total of 45-60 minutes, using all of solution (1) in the first 15-20 minutes.

2. After the last wash in solution (2), remove the membrane pieces from the tube, identify each piece, and place into a separate PCR tube.

When all wash solution is used up, tip out the filters into a Petri dish. Identify each filter and place into its own PCR tube;

3. Denaturation

Bound probes are released by heat denaturation in 1×PCR mix. Add 50 µl aliquots of 1×PCR mix (e.g., Advanced Biotechnologies buffer IV) to each PCR tube. into thin-walled 200 µl PCR tubes, and add the filter, transferring as little as possible of the washing solution with it denature for 5 minutes at 95° C. The resulting solution contains the eluted reference and target probes that were hybridized to the sample nucleic acid sample. Eluted probes are then placed under conditions that permit annealing of the complementary target and reference tag sequences, e.g., 1×PCR buffer at 45° C.

Following annealing of target and reference probes to each other, streptavidin coated beads are introduced to promote the binding of the biotin label on the reference primer to the beads under binding conditions. After the biotin has bound to the beads, the solution is spun down in a microcentrifuge and the supernatant with the unbound target probes is collected for analysis.

A sample (e.g., 5 µl) of the supernatant with the unbound target probes is then used as template in a PCR reaction. This is a plus/minus PCR reaction testing only for the presence of significant amounts of the target probe. Exemplary PCR cycling conditions are as follows:

a. 95° C. for 10 minutes (activate enzyme)

b. Cycle 50 times the following:
  i. 94° C. for 30 seconds
  ii. 55° C. for 30 seconds
  iii. 72° C. for 60 seconds c. Hold at 72° C. for 15 seconds d. Ramp from 72° C.-99° C. rising by 1° C. over 5 seconds Recovered probes are then paired and cross-linked as described below.

Probe Pairing and Pair Cross-linking:

The filters are removed from the solutions leaving only the retrieved probe mixtures. Retrieved probes are then placed under conditions that permit annealing and crosslinking of the complementary target and reference tag sequences by a specially designed mitomycin dimer (Mitomycin Dimer 5 shown below from Paz et al, J. Med. Chem. 2004, 47, 3308-3319), in e.g., low pH or reductive buffer at 37° C.

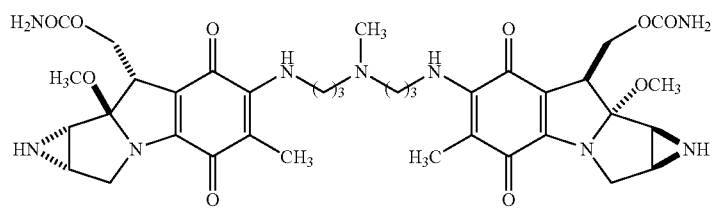

Example 2

Detection of the Amount of a Chromosome 18 Sequence Relative to a Chromosome 10 Sequence Using Crosslinking The methods described herein were applied to the detection of trisomy 18 in maternal serum. The test and reference probes used were as follows:

Test Probe:

```
                                        (SEQ ID NO: 7)
5'-[6-FAM]CCATG GGAAC AGAGA AACCT GCGTG TGAGG

TGTCA GCATG AGGAG ACCA TCGTC GTCGT CGTTC GTCGT-3'
```

Reference Probe:

```
                                        (SEQ ID NO: 8)
5'-[6-FAM]ACGC TTTTA TGGGC TCTGA TGACC GAGGT

CTCAA TGTCG ATTGG GTGGT ACGAC GAACG ACGAC GACGA-3'
```

Interfering Primers:

```
5'- AC GAACG ACGAC GACGA-3'    (SEQ ID NO: 9)

5'- TC GTCGT CGTTC GTCGT-3'    (SEQ ID NO: 10)
```

The last 20 nucleic acids of the test probe (bold) are the complement of the last 20 nucleic acids of the reference probe (flipped and complemented). This complementary segment also contains several CGACG sequences at the 3' end of the reference probe.

Each of these probes carry fluorescent tags, e.g., 6-FAM, permitting quantification by capillary electrophoresis for controls. The 6-FAM tags do not participate in the reactions.

In this method, one starts with high molecular weight genomic DNA, at relatively high concentration (>0.1 mg/ml) and a probe mix with both the target and the reference probe and excess interfering primers are added.

Hybridization Washing and Probe Elution:

Membranes containing sample nucleic acid are prepared, pre-hybridized, hybridized and washed as in Example 1, above. Hybridized probes are eluted as in Example 1.

After sufficient crosslinking, PCR conditions are reestablished either by sufficient adjusting of the buffer or by alcohol precipitation of the DNA followed by resuspension.

Detection:

A sample (e.g., 5 µl) of the resulting mixture of free and crosslinked probes is then used as template in a PCR reaction. This ise a PCR reaction testing for both the presence of the reference and the target probe. Exemplary PCR cycling conditions are as follows:

e. 95° C. for 10 minutes (activate enzyme)

f. Cycle 50 times the following:
  i. 94° C. for 30 seconds
  ii. 55° C. for 30 seconds
  iii. 72° C. for 60 seconds g. Hold at 72° C. for 15 seconds h. Ramp from 72° C.-99° C. rising by 1° C. over 5 seconds

Example 3

Detection of the Amount of a Chromosome X Sequence Relative to a Chromosome 10 Sequence Using Biotin Immobilization of the Pairs The methods described herein were applied to the detection of triple X in maternal serum. The test and reference probes used were as follows:

Single Probe:

```
                                        (SEQ ID NO: 11)
5'-CTCTC TGCAA AGCCT CCTAG CCCGG TTCTC CAGCC

CTCCC CAGAC CAAT TATAT [Bio-T] ATATA ACGC TTTTA

TGGGC TCTGA TGACC GAGGT CTCAA TGTCG ATTGG GTGGT-3'
```

The first 49 nucleotides in the single probe are complementary to chromosome X. The last 49 nucleotides are complementary to chromosome 10. The middle 10 nucleic acids of the single probe (bold) are a nonsense linking sequence and an intrastrand biotin.

The biotin label can be used to remove paired probes.

In this method, one starts with fragmented genomic DNA, at a known concentration (>0.1 mg/ml) and a probe mix.

Hybridization

The genomic DNA is incubated with a probe mix where Chromosome 10 and the probe is assumed to be equimolar. This mixture is then placed under conditions that permit annealing of the complementary target and reference tag sequences, e.g., 1× PCR buffer at 45° C.

Following annealing of target and reference probes to each other, streptavidin coated beads are introduced to promote the binding of the biotin label on the probe to the beads under binding conditions. After the biotin has bound to the beads, the solution is spun down in a microcentrifuge and the supernatant with the unbound genomic DNA is collected for analysis.

A sample (e.g., 5 μl) of the supernatant with the unbound genomic DNA is then used as template in a PCR reaction. This is a PCR reaction testing for the relative amount of the target and the reference sequence on chromosomes X and 10 respectively. Exemplary PCR cycling conditions are as follows:

i. 95° C. for 10 minutes (activate enzyme)
j. Cycle 50 times the following:
  i. 94° C. for 30 seconds
  ii. 55° C. for 30 seconds
  iii. 72° C. for 60 seconds
k. Hold at 72° C. for 15 seconds
l. Ramp from 72° C.-99° C. rising by 1° C. over 5 seconds

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

The invention claimed is:

1. A method of determining the amount of a target nucleic acid relative to the amount of a reference nucleic acid in a nucleic acid sample, comprising:
   A) incubating said sample under conditions that permit specific binding of first and second probes to said target and reference nucleic acids, respectively, wherein
      (i) said nucleic acid sample comprises said target and reference nucleic acids;
      (ii) said first probe comprises a target nucleic acid binding sequence and a second probe binding moiety;
      (iii) said second probe comprises a reference nucleic acid binding sequence and a first probe binding moiety;
   B) placing said first and second probes under conditions that permit the pairing of said probes, wherein said pairing comprises binding of said first probe binding moiety to said second probe binding moiety, to form paired probes; and
   C) detecting unpaired probe, wherein said detecting is indicative of a difference in the amount of target and reference nucleic acids in said sample.

2. The method of claim 1, further comprising removing un-hybridized probes after step (A).

3. The method of claim 1, further comprising denaturing the hybridized probes after step (A).

4. A method of determining the amount of a target nucleic acid sequence relative to the amount of a reference nucleic acid sequence in a nucleic acid sample, the method comprising:

(a) providing a sample, said sample comprising said target nucleic acid sequence and said reference nucleic acid sequence;
(b) contacting said sample, under conditions that permit hybridization, with first and second probes that have the following characteristics:
   (i) said first probe comprises a first binding partner moiety and a sequence that binds specifically to said target nucleic acid sequence, wherein said first binding partner moiety can bind a second binding partner moiety on said second probe when said probes are placed under conditions that permit binding of said binding partner moieties; and
   (ii) said second probe comprises a second binding partner moiety and a sequence that binds specifically to said reference nucleic acid sequence;
(c) placing said first and second probes of step (b) under conditions that permit said first binding partner moiety of said first probe to interact with said second binding partner moiety of said second probe such that said first and second probes become bound to each other to form paired probes; and
(d) detecting a probe that is not bound to another probe, wherein said detecting indicates a difference in the amount of target and reference nucleic acid sequences present in said sample.

5. The method of claim 4, further comprising removing un-hybridized probes after step (b).

6. The method of claim 4, further comprising denaturing the hybridized probes after step (b).

7. The method of claim 1 wherein, prior to said detecting, the method comprises the step of removing paired probes or rendering paired probes resistant to detection.

8. The method of claim 7 wherein said step of removing paired probes or rendering paired probes resistant to detection comprises cross-linking said probes.

9. The method of claim 8 wherein said cross-linking comprises U.V. cross-linking or chemical cross-linking.

10. The method of claim 1, wherein said first or second probe comprises a chemically modified nucleotide.

11. The method of claim 10, wherein said chemically modified nucleotide is a halogenated nucleotide.

12. The method of claim 10, wherein said chemically modified nucleotide is a thiol modified nucleotide.

13. The method of claim 10, wherein said chemically modified nucleotide is an amino modified nucleotide.

14. The method of claim 10, wherein said chemically modified nucleotide is a biotinylated nucleotide.

15. The method of claim 10, wherein said chemically modified nucleotide is present in a said first or second binding partner moiety.

16. The method of claim 10, wherein said chemically modified nucleotide permits cross-linking of said first and second binding partner moieties.

17. The method of claim 1 wherein said step of detecting unpaired probe comprises PCR amplification of a probe, target or reference nucleic acid sequence.

18. The method of claim 1, wherein said step of detecting unpaired probe comprises the steps of cross linking to each other probes that are bound to each other, and amplifying a probe sequence, wherein cross-linked probes are not amplified.

19. The method of claim 1, wherein said first and second probes comprise single stranded nucleic acids.

20. The method of claim 1, wherein said first probe and said second probe interact via an adapter molecule.

21. The method of claim 1, wherein said first and second probes do not comprise a detectable label.

22. The method of claim 1, wherein at least one of said first and second probe further comprises a detectable label.

23. The method of claim 1, wherein said first and second probe do not comprise a hairpin structure.

24. The method of claim 1, wherein said first or said second probe is resistant to nuclease cleavage.

25. The method of claim 1, wherein said sample is obtained at least partially from serum or plasma.

26. The method of claim 1, wherein said sample is obtained at least partially from a biopsy specimen.

27. The method of claim 1, wherein said sample is obtained at least partially from a biological fluid.

28. The method of claim 1, wherein said sample is obtained at least partially from a swab or smear.

29. The method of claim 1, wherein said sample is obtained at least partially from cell culture.

30. The method of claim 1, wherein said sample is obtained at least partially from RNA or cDNA.

31. The method of claim 1, wherein said sample is obtained at least partially through synthesis.

32. The method of claim 1, wherein said pairing comprises the binding of said first and second probes to each other in a specific, predefined ratio.

33. The method of claim 32 wherein said specific predefined ratio is 1:1.

34. The method of claim 1, wherein said nucleic acid sample is immobilized on a solid support.

35. The method of claim 1, wherein said first probe and said second probe are contacted with said nucleic acid sample sequentially.

36. The method of claim 1, wherein said first and second probe binding moieties comprise nucleic acid sequences that can hybridize to each other.

37. The method of claim 36 wherein said sequence of said first probe binding moiety is complementary to a sequence adjacent to the reference sequence in said nucleic acid sample.

38. The method of claim 1, wherein said second probe further comprises an additional tag moiety that can mediate selective binding to a solid support or to a specific binding partner.

39. The method of claim 38 wherein said step of detecting comprises immobilizing said second probe to a solid support via said additional tag moiety, whereby first probe that is bound to said second probe is selectively removed.

40. The method of claim 39 wherein said solid support comprises a bead or particle.

41. The method of claim 38 wherein said tag moiety is a member of a specific binding pair.

42. The method of claim 38 wherein said tag comprises biotin.

43. The method of claim 3, further comprising the step of placing said denatured probes under conditions that permit said probe binding moiety of said first probe to bind said probe binding moiety of said second probe.

44. The method of claim 43 wherein said step of placing said denatured probes under conditions that permit said probe binding moiety of said first probe to bind said probe binding moiety of said second probe comprises one or more of placing said denatured probes under conditions that permit said probe binding moiety of said first probe to bind said probe binding moiety of said second probe comprises placing said probes under conditions that permit hybridization, changing temperature, altering pH or salt concentration, and UV irradiation.

45. The method of claim 1, wherein said first and/or said second probes comprise a fluorescent or radioactive label.

46. The method of claim 1, wherein said detecting comprises capillary electrophoresis.

47. The method of claim 1, wherein said detecting comprises measurement of fluorescence, radioactivity or enzyme activity.

48. The method of claim 1, wherein said nucleic acid sample comprises genomic DNA.

49. The method of claim 1, wherein said nucleic acid sample comprises RNA.

50. The method of claim 1, wherein said nucleic acid sample comprises cDNA.

51. The method of claim 1, wherein said serum or plasma is obtained from a pregnant woman, and wherein said method detects a difference in the amount of a fetal nucleic acid sequence.

52. A method of determining the amount of a target nucleic acid relative to the amount of a reference nucleic acid in a nucleic acid sample, the method comprising:
(a) contacting a nucleic acid sample with a probe under conditions that permit hybridization, wherein said probe comprises a sequence that specifically binds to said target nucleic acid sequence and a sequence that specifically binds to said reference nucleic acid sequence;
(b) detecting unhybridized probe, target or reference nucleic acid, wherein hybridized probe and/or target and/or reference nucleic acid is resistant to detection, and wherein said detecting determines the amount of said target nucleic acid relative to the amount of said reference nucleic acid present in said nucleic acid sample.

53. The method of claim 52 comprising removing or rendering hybridized probes generated in step (a) resistant to detection.

54. The method of claim 53 wherein said step of removing or rendering hybridized probes resistant to detection comprises cross-linking probe hybrids generated in step (a).

55. The method of claim 52 wherein said step of detecting comprises PCR amplification of an unhybridized probe, target or reference nucleic acid sequence.

56. The method of claim 52, wherein said step of detecting comprises the steps of cross linking hybridized probes to reference and target sequences to which they are hybridized, and amplifying a probe, reference or target sequence, wherein cross-linked sequences are not amplified.

57. A method of detecting a chromosomal abnormality, said method comprising the steps of
   (a) obtaining a nucleic acid sample;
   (b) contacting said sample, under conditions that permit hybridization, with first and second probes that have the following characteristics:
      (i) said first probe comprises a sequence that binds specifically to said target sequence, and a first binding partner moiety, wherein said first binding partner moiety can bind a second binding partner moiety on said second probe, when said probes are placed under conditions that permit binding of said binding partner moieties; and
      (ii) said second probe comprises a sequence that binds specifically to said reference sequence and said second binding partner moiety, wherein said first and second probes hybridize to target and reference nucleic acid sequences, respectively, present in said sample;
   (c) placing said hybridized probes under conditions that permit said binding partner moiety of said first probe to bind said binding partner moiety of said second probe, such that said first and second probes become bound to each other; and
   (d) detecting a probe that is not bound to another probe, wherein said detecting indicates a difference in the amount of target and reference nucleic acid sequences present in said sample, wherein said difference indicates the presence of a genetic abnormality.

58. The method of claim 57 wherein said nucleic acid sample is obtained from serum or plasma.

59. The method of claim 57, further comprising removing un-hybridized probes after step (b).

60. The method of claim 57, further comprising denaturing the hybridized probes after step (b).

61. The method of claim 57, wherein said serum is obtained from a pregnant woman and wherein said method detects a chromosomal abnormality in her fetus.

62. The method of claim 61 wherein said chromosomal abnormality is an anueploidy.

63. The method of claim 57 wherein said genetic abnormality is a chromosomal abnormality.

64. The method of claim 63 wherein said chromosomal abnormality is a chromosomal deletion or chromosomal duplication.

65. The method of claim 57 wherein said genetic abnormality is an autosomal recessive disorder.

66. The method of claim 57 wherein said genetic abnormality is aneuploidy, chromosomal deletion or duplication associated with cancer.

67. The method of claim 57 wherein said nucleic acid sample is obtained from an individual suspected or known to have cancer.

68. A method of detecting a chromosomal abnormality, the method comprising:
   (a) contacting a nucleic acid sample with a probe under conditions that permit hybridization, wherein said probe comprises a sequence that specifically binds to said target nucleic acid sequence and a sequence that specifically binds to said reference nucleic acid sequence;
   (b) removing or rendering hybridized probes generated in step (a) resistant to detection; and
   (c) detecting unhybridized probe, target or reference nucleic acid, wherein said detecting determines the amount of said target nucleic acid relative to the amount of said reference nucleic acid present in said nucleic acid sample.

69. The method of claim 68 wherein said sample is obtained from serum or plasma.

70. The method of claim 68 wherein said step of removing or rendering hybridized probes resistant to detection comprises cross-linking probe hybrids generated in step (a).

71. The method of claim 68 wherein said step of detecting comprises PCR amplification of an unhybridized probe, target or reference nucleic acid sequence.

72. The method of claim 68, wherein said step of detecting comprises the steps of cross linking hybridized probes to reference and target sequences to which they are hybridized, and amplifying a probe, reference or target sequence, wherein cross-linked sequences are not amplified.

* * * * *

SEQUENCE LISTING

```
<160> NUMBER OF SEQ ID NOS: 11

<210> SEQ ID NO 1
<211> LENGTH: 97
<212> TYPE: DNA
<213> ORGANISM: Artificial Sequence
<220> FEATURE:
<223> OTHER INFORMATION: Synthetic oligo probe for human Chromosome 21,
      including addition al sequence for pairing with a reference probe.

<400> SEQUENCE: 1
cgtgaagttc tgtggacagt agtgcttgtc tgtggtcagc cctgggctca acggggctgc      60
ctcagagaag ctgctgagga ccacccaatc gacattg                              97

<210> SEQ ID NO 2
<211> LENGTH: 82
<212> TYPE: DNA
<213> ORGANISM: Artificial Sequence
<220> FEATURE:
<223> OTHER INFORMATION: Synthetic oligo probe for human chromosome 10
      sequence, including additional sequence for pairing with a test
      probe.

<400> SEQUENCE: 2
acaagctgca agctcacgac ttaccattcc gtaacgcttt tatgggctct gatgaccgag      60
gtctcaatgt cgattgggtg gt                                              82

<210> SEQ ID NO 3
<211> LENGTH: 49
<212> TYPE: DNA
<213> ORGANISM: Artificial Sequence
<220> FEATURE:
<223> OTHER INFORMATION: Synthetic oligonucleotide reference probe for
      human Chromosome 10p including sequence for pairing with a test
      probe.

<400> SEQUENCE: 3
acgcttttat gggctctgat gaccgaggtc tcaatgtcga ttgggtggt                  49

<210> SEQ ID NO 4
<211> LENGTH: 69
<212> TYPE: DNA
<213> ORGANISM: Artificial Sequence
```

```
<220> FEATURE:
<223> OTHER INFORMATION: Synthetic oligonucleotide probe for human
      chromosome 21q, including sequence for pairing with a reference
      probe.

<400> SEQUENCE: 4
tggtactttt agggaaaac gtgatgtgtg gactgtatcc caaggcctta ccacccaatc    60
gacattgag                                                           69

<210> SEQ ID NO 5
<211> LENGTH: 69
<212> TYPE: DNA
<213> ORGANISM: Artificial sequence
<220> FEATURE:
<223> OTHER INFORMATION: Synthetic oligonucleotide probe for human X
      chromosome, including sequence for pairing with a reference probe.

<400> SEQUENCE: 5
ctctctgcaa agcctcctag cccggttctc cagccctccc cagaccaata ccacccaatc   60
gacattgag                                                           69

<210> SEQ ID NO 6
<211> LENGTH: 69
<212> TYPE: DNA
<213> ORGANISM: Artificial sequence
<220> FEATURE:
<223> OTHER INFORMATION: Synthetic oligonucleotide probe for human
      chromosome 18, including sequence for pairing with a reference
      probe.

<400> SEQUENCE: 6
ccatgggaac agagaaacct gcgtgtgagg tgtcagcatg aggagaccaa ccacccaatc   60
gacattgag                                                           69

<210> SEQ ID NO 7
<211> LENGTH: 69
<212> TYPE: DNA
<213> ORGANISM: Artificial sequence
<220> FEATURE:
<223> OTHER INFORMATION: Synthetic oligonucleotide probe for human
      chromosome 18, including sequence for pairing with a reference
      probe.

<400> SEQUENCE: 7
ccatgggaac agagaaacct gcgtgtgagg tgtcagcatg aggagaccat cgtcgtcgtc   60
gttcgtcgt                                                           69

<210> SEQ ID NO 8
<211> LENGTH: 69
<212> TYPE: DNA
<213> ORGANISM: Artificial sequence
<220> FEATURE:
<223> OTHER INFORMATION: Synthetic oligonucleotide probe for human
      chromosome 10, including sequence for pairing with a test probe.

<400> SEQUENCE: 8
acgcttttat gggctctgat gaccgaggtc tcaatgtcga ttgggtggta cgacgaacga   60
cgacgacga                                                           69

<210> SEQ ID NO 9
<211> LENGTH: 17
<212> TYPE: DNA
<213> ORGANISM: Artificial sequence
<220> FEATURE:
```

-continued

```
<223> OTHER INFORMATION: Synthetic PCR interfering oligonucleotide that
      hybridizes to test probe.

<400> SEQUENCE: 9
acgaacgacg acgacga                                                   17

<210> SEQ ID NO 10
<211> LENGTH: 17
<212> TYPE: DNA
<213> ORGANISM: Artificial sequence
<220> FEATURE:
<223> OTHER INFORMATION: Synthetic interfering oligonucleotide that
      hybridizes to reference probe.

<400> SEQUENCE: 10
tcgtcgtcgt tcgtcgt                                                   17

<210> SEQ ID NO 11
<211> LENGTH: 108
<212> TYPE: DNA
<213> ORGANISM: Artificial sequence
<220> FEATURE:
<223> OTHER INFORMATION: Synthetic oligonucleotide probe for human X
      chromosome, including reference sequence that hybridizes to human
      chromosome 10 sequences.

<400> SEQUENCE: 11
ctctctgcaa agcctcctag cccggttctc cagccctccc cagaccaatt atatatataa    60
cgcttttatg ggctctgatg accgaggtct caatgtcgat tgggtggt                108
```